(12) United States Patent
Blanz

(10) Patent No.: US 7,339,374 B2
(45) Date of Patent: Mar. 4, 2008

(54) CORRECTION OF NMR ARTIFACTS DUE TO AXIAL MOTION AND SPIN-LATTICE RELAXATION

(75) Inventor: Martin Blanz, Celle (DE)

(73) Assignee: Baker Hughes Incorporated, Houston, TX (US)

( * ) Notice: Subject to any disclaimer, the term of this patent is extended or adjusted under 35 U.S.C. 154(b) by 0 days.

(21) Appl. No.: 11/752,419

(22) Filed: May 23, 2007

(65) Prior Publication Data

US 2007/0222443 A1 Sep. 27, 2007

Related U.S. Application Data

(63) Continuation of application No. 11/435,265, filed on May 16, 2006.

(51) Int. Cl.
G01V 3/00 (2006.01)
(52) U.S. Cl. .......................... 324/303; 324/300
(58) Field of Classification Search ............... 324/300, 324/303; 175/27; 702/6, 7
See application file for complete search history.

(56) References Cited

U.S. PATENT DOCUMENTS

| | | | |
|---|---|---|---|
| 5,055,787 A | 10/1991 | Kleinberg et al. | 324/303 |
| 5,280,243 A | 1/1994 | Miller | 324/303 |
| 5,389,877 A | 2/1995 | Sezginer et al. | 324/303 |
| 5,557,201 A | 9/1996 | Kleinberg et al. | 324/303 |
| 5,698,979 A | 12/1997 | Taicher et al. | 324/303 |
| 5,705,927 A | 1/1998 | Sezginer et al. | 702/6 |
| 5,867,806 A | 2/1999 | Strickland et al. | 702/7 |
| 6,215,304 B1 | 4/2001 | Slade | 324/303 |
| 6,268,726 B1 | 7/2001 | Prammer et al. | 324/303 |
| 6,297,632 B1 | 10/2001 | Speier | 324/303 |
| 6,392,409 B1 * | 5/2002 | Chen | 324/303 |
| 6,459,263 B2 | 10/2002 | Hawkes et al. | 324/303 |
| 6,466,013 B1 | 10/2002 | Hawkes et al. | 324/303 |
| 6,518,757 B1 * | 2/2003 | Speier | 324/303 |
| 6,566,874 B1 | 5/2003 | Speier et al. | 324/303 |
| 6,600,316 B2 * | 7/2003 | Chen et al. | 324/303 |
| 6,769,497 B2 | 8/2004 | Dubinsky et al. | 175/27 |
| 7,135,862 B2 * | 11/2006 | Hagiwara | 324/303 |
| 2002/0153888 A1 | 10/2002 | Kruspe et al. | 324/303 |
| 2002/0163334 A1 * | 11/2002 | Hagiwara | 324/303 |
| 2003/0132749 A1 | 7/2003 | Speier et al. | 324/303 |
| 2005/0088176 A1 | 4/2005 | Kruspe et al. | 324/303 |
| 2006/0273787 A1 * | 12/2006 | Blanz | 324/303 |
| 2007/0222443 A1 * | 9/2007 | Blanz | 324/303 |

FOREIGN PATENT DOCUMENTS

| | | |
|---|---|---|
| EP | 0977057 A2 | 2/2000 |
| WO | WO03001693 A1 | 2/2003 |

* cited by examiner

*Primary Examiner*—Brij Shrivastav
(74) *Attorney, Agent, or Firm*—Madan, Mossman & Sriram, P.C.

(57) ABSTRACT

NMR spin echo signals are corrected for axial motion of the borehole logging tool. The correction is applied to an averaged echo train using an average velocity determined from surface measurements over the duration of averaging of the echo trains. An additional correction may be applied to correct for excess polarization or incomplete polarization of nuclear spins due to an insufficient wait time between pulse sequences. It is emphasized that this abstract is provided to comply with the rules requiring an abstract which will allow a searcher or other reader to quickly ascertain the subject matter of the technical disclosure. It is submitted with the understanding that it will not be used to interpret or limit the scope or meaning of the claims.

20 Claims, 17 Drawing Sheets

CORRECTION OF NMR ARTIFACTS DUE TO AXIAL MOTION AND SPIN-LATTICE RELAXATION

CROSS-REFERENCES TO RELATED APPLICATIONS

This application is a continuation of U.S. patent application Ser. No. 11/435,265, now pending, which is a continuation-in-part of U.S. patent application Ser. No. 10/918,965, now U.S. Pat. No. 7,196,516.

BACKGROUND OF THE INVENTION

1. Field of the Invention

The present invention relates generally to determining geological properties of subsurface formations using Nuclear Magnetic Resonance ("NMR") methods for logging wellbores, particularly for correcting for the effects of tool motion and pulse sequence timing on NMR signals.

2. Description of the Related Art

A variety of techniques are currently utilized in determining the presence and estimation of quantities of hydrocarbons (oil and gas) in earth formations. These methods are designed to determine formation parameters, including among other things, the resistivity, porosity and permeability of the rock formation surrounding the wellbore drilled for recovering the hydrocarbons. Typically, the tools designed to provide the desired information are used to log the wellbore. Much of the logging is done after the well bores have been drilled. More recently, wellbores have been logged while drilling, which is referred to as measurement-while-drilling (MWD) or logging-while-drilling (LWD).

One commonly used technique involves utilizing Nuclear Magnetic Resonance (NMR) logging tools and methods for determining, among other things, porosity, hydrocarbon saturation and permeability of the rock formations. The NMR logging tools are utilized to excite the nuclei of the liquids in the geological formations surrounding the wellbore so that certain parameters such as nuclear spin density, longitudinal relaxation time (generally referred to in the art as $T_1$) and transverse relaxation time (generally referred to as $T_2$) of the geological formations can be measured. From such measurements, porosity, permeability and hydrocarbon saturation are determined, which provides valuable information about the make-up of the geological formations and the amount of extractable hydrocarbons.

The NMR tools generate a static magnetic field in a region of interest surrounding the wellbore. NMR is based on the fact that the nuclei of many elements have angular momentum (spin) and a magnetic moment. The nuclei have a characteristic Larmor resonant frequency related to the magnitude of the magnetic field in their locality. Over time the nuclear spins align themselves along an externally applied static magnetic field creating a net magnetization. This equilibrium situation can be disturbed by a pulse of an oscillating magnetic field, which tips the spins with resonant frequency within the bandwidth of the oscillating magnetic field away from the static field direction. The angle θ through which the spins exactly on resonance are tipped is given by the equation:

$$\theta = \gamma B_1 t_p / 2 \quad (1)$$

where γ is the gyromagnetic ratio, $B_1$, is the magnetic flux density amplitude of the sinusoidally oscillating field and $t_p$ is the duration of the RF pulse.

After tipping, the spins precess around the static field at a particular frequency known as the Larmor frequency $\omega_0$ given by $$\omega_0 = \gamma B_0 \quad (2)$$

where $B_0$ is the static magnetic flux density. For hydrogen nuclei γ/2π=4258 Hz/Gauss, so that a static field of 235 Gauss, would produce a precession frequency of 1 MHz. At the same time, the magnetization returns to the equilibrium direction (i.e., aligned with the static field) according to a decay time known as the "spin-lattice relaxation time" or $T_1$. $T_1$ is controlled by the molecular environment and is typically ten to one thousand milliseconds in rocks.

At the end of a θ=90° tipping pulse, spins on resonance are pointed in a common direction perpendicular to the static field, and they precess at the Larmor frequency. However, because of inhomogeneity in the static field due to the constraints on tool shape, imperfect instrumentation, or microscopic material heterogeneities, each nuclear spin precesses at a slightly different rate. Hence, after a time long compared to the precession period, but shorter than $T_1$, the spins will no longer be precessing in phase. This de-phasing occurs with a time constant that is commonly referred to as $T_2^*$. Dephasing due to static field inhomogeneity can be recovered by generating spin echoes (see below). The remaining dephasing is characterized by the time constant $T_2$ and is due to properties of the material.

A receiving coil is designed so that a voltage is induced by the precessing spins. Only that component of the nuclear magnetization that is precessing in the plane perpendicular to the static field is sensed by the coil. After a 180° tipping pulse (an "inversion pulse"), the spins on resonance are aligned opposite to the static field and the magnetization relaxes along the static field axis to the equilibrium direction. Hence, a signal will be generated after a 90° tipping pulse, but not after a 180° tipping pulse in a generally uniform magnetic field.

While many different methods for measuring $T_1$ have been developed, a single standard known as the CPMG sequence (Carr-Purcell-Meiboom-Gill) for measuring $T_2$ has evolved. In contrast to laboratory NMR magnets, well logging tools have inhomogeneous magnetic fields due to the constraints on placing the magnets within a tubular tool and the inherent "inside-out" geometry. Maxwell's divergence theorem dictates that there cannot be an extended region of high homogeneity outside the tool. Therefore in typical well bores, $T_2^* \ll T_2$, and the free induction decay becomes a measurement of the apparatus-induced inhomogeneities. To measure the true $T_2$ in such situations, it is necessary to cancel the effect of the apparatus-induced inhomogeneities. To accomplish the same, a series of pulses is applied to repeatedly refocus the spin system, canceling the $T_2^*$ effects and forming a series of spin echoes. The decay of echo amplitude is a true measure of the decay due to material properties. Furthermore it can be shown that the decay is in fact composed of a number of different decay components forming a $T_2$ distribution. The echo decay data can be processed to reveal this distribution which is related to rock pore size distribution and other parameters of interest to the well log analyst.

Tool motion can seriously affect the performance of NMR tools used in an MWD environment. NMR tools that have static magnetic fields with complete rotational symmetry are unaffected by rotation of the tool since the fields in the region of examination do not change during the measurement sequence. However, any axial or transverse (orthogonal to the tool axis) component of tool motion will affect the NMR signal.

There are many well-known artifacts of motion that show up in signals in downhole logging. These artifacts are theoretically expected and are attributable to such factors as rotation, transverse vibration and axial motion. In addition to these motion artifacts the NMR signal amplitude can be reduced due to insufficient wait time for polarization after the end of an echo sequence.

Artifacts of rotation are a result of the typical stationary $B_0$ field of the system not being completely axisymmetric. Rotation of the drillstring therefore causes (periodic) NMR signal losses during a spin echo train. Artifacts from transverse vibrations generally occur because of drilling or because of mud circulation through a mud motor. The obtained vibration frequency spectrum usually includes some dominant frequencies that are directly related to the rotational speed of the motor or drill string.

Axial motion of the drill string gives rise to two distinct artifacts. A first artifact of axial motion is caused by the motion of the drillstring through the borehole. The rate of penetration (ROP) of the drill string can be recorded electronically and later retrieved from a computer file. Obviously, the ROP at the drill bit differs slightly from the electronically-recorded value of the ROP which is measured at the surface. This discrepancy between ROP values is due to limited time resolution of the computer file as well as to flexibility of the drill string. A second artifact of axial motion exhibits itself as higher frequency axial vibrations. These vibrations can be measured with an accelerometer in the NMR tool.

Application of an insufficient wait time between consecutive pulse sequences can give rise to yet another artifact. Typically, after the end of an echo sequence obtained with axial motion of the drill string, the z-magnetization is substantially zero. This z-magnetization is generally non-zero when no such motion exists. A wait time is generally applied after an echo sequence to allow the protons to re-align along the direction of the static magnetic field. This re-magnetization occurs with a characteristic relaxation time known as the spin-lattice relaxation time $T_1$. Usually, there exists a distribution of $T_1$ times similar to the well-known $T_2$ distribution.

U.S. Pat. No. 5,389,877 issued to Sezginer describes a truncated CPMG sequence in which the sequence duration and recovery delay are so short that only signals from the clay and capillary bound fluids are detected. A truncated sequence has the advantage that the effect of tool motion on the measurements is reduced due to the short measurement time (approx. 50 ms, compared to greater than 300 ms for normal downhole CPMG measurements.) As discussed in U.S. Pat. No. 5,705,927 issued to Kleinberg, resonance regions of many prior art instruments are of the order of 1 mm. Accordingly, a lateral vibration at a frequency of 50 Hz having an amplitude of 1 mm (10 g acceleration) would disable the instrument. The Kleinberg '927 patent discloses making the length of each CPMG sequence small, e.g. 10 ms, so that the drill collar cannot be displaced by a significant fraction of the vertical or radial extent of the sensitive region during a CPMG pulse sequence. However, as noted above, using such short sequences and short wait times only gives an indication of the bound fluid volume and gives no indication of the total fluid volume.

U.S. Pat. No. 6,268,726 to Prammer et al., teaches the use of motion sensors on an MWD apparatus that makes measurements of tool motion of a NMR sensor assembly. Measurements are made by the NMR sensor during continued drilling operations, and subsequently, the measurements made by the motion sensor are used to select a subset of the NMR measurements that meet certain requirements on tool motion and hence would be expected to give a reasonable insensitivity to tool motion. U.S. Pat. No. 6,459,263 to Hawkes et al, having the same assignee as the present application and the contents of which are fully incorporated herein by reference, uses the output of motion sensors in combination with predictive filtering to control the timing of pulses for a modified (as in the Hawkes '013 patent) or conventional CPMG sequence.

U.S. Pat. No. 6,566,874 to Speier et al. teaches several approaches to dealing with problems associated with tool motion. In one embodiment, measurements are made of two different echo trains that have different sensitivities to tool motion. A tool is used having two different regions of examination: a high gradient zone defined by one set of magnets and antennas, and a low gradient zone defined by another set of magnets and antennas. The effect of tool motion on the signal amplitude is greater in the high gradient zone than in the low gradient zone. Using these two sets of signals and knowing the gradients of the respective zones, it is possible to estimate what the signal would have been without the tool motion. The Speier '874 patent also teaches that sensitivity to motion may be varied by different field geometries with different gradients. This requirement of having two different regions of examination complicates the hardware. Another drawback (noted in Speier '874) to the above-described techniques is that the measurements must be separated in time and/or space. In order to interpret the results it is assumed that, in the absence of motion, the NMR signal (and therefore the formation measured) is the same in both measurements. For a continuously moving logging tool, this condition is not always given. Also the motion during the two measurements should be the same, or at least have the same characteristics.

In another embodiment taught by Speier '874, measurements are processed to obtain both the $T_1$ and $T_2$ distribution. The effect of tool motion is different on the two types of measurements. This approach has at least two drawbacks. The first is that $T_1$ determination is time consuming. A second drawback is that in the absence of an exact knowledge of the ratio of $T_1/T_2$, the method can only be used for quality control and not for determining both the $T_1$ and $T_2$ distributions.

U.S. patent application Ser. No. 10/918,965 of Blanz et al. discloses a method of processing and an apparatus used for processing Nuclear Magnetic Resonance (NMR) signals from an earth formation. The spin echo signals are corrected using a function of the velocity to give corrected spin echo signals. The correction may be implemented by scaling the spin echo signals by a normalizing function related to the axial velocity and a reference velocity. The correction factor may be applied to the in-phase component, quadrature component or to the amplitude of the spin echo signals of a spin echo sequence. The invention of Blanz uses measurements or estimates of the axial velocity in applying the correction. Such measurements or estimates of the downhole axial velocity may be difficult to obtain. There is a need for computational methods to reduce the effects of motion artifacts encountered in MWD testing without using the downhole axial velocity

SUMMARY OF THE INVENTION

The present invention is a method of processing and an apparatus used for processing Nuclear Magnetic Resonance (NMR) signals from an earth formation. The NMR tool is conveyed into a borehole in the earth formation and moved with an axial velocity in the borehole. Nuclear spins in the earth formations are polarized. An antenna on the NMR logging tool is pulsed with a pulse sequence to produce a plurality of spin echo trains. The echo trains are averaged to give an averaged echo train. The averaged echo train is corrected using a function of the average velocity to give a corrected echo train. The NMR logging tool may be conveyed into the borehole on a wireline, slickline, drillstring, or coiled tubing. The correction may be implemented by scaling the spin echo signals by a normalizing function related to the average axial velocity and a reference velocity. The correction factor may be applied to the in-phase component, quadrature component or to the amplitude of the spin echo signals. The first correction compensates for one type of effects caused by tool motion. A second correction may be applied to compensate for the excessive premagnetization and also for insufficient wait time that would not allow full magnetization of the nuclei used for NMR. This second correction may be in addition to or applied independently of the first correction. The second correction is calculated for the longitudinal relaxation values corresponding to the bins of the $T_2$ distribution. The second correction is then executed by multiplying each bin of the $T_2$ distribution by its correction factor. The result is a T2 distribution where constant axial velocity artifacts and insufficient recovery time artifacts have been eliminated.

In one embodiment of the invention, a plurality of pulse sequences is applied with a wait time therebetween. A second correction may be applied to compensate for the excessive premagnetization and also for insufficient wait time that would not allow full magnetization of the nuclei used for NMR. This second correction may be in addition to or applied independently of the first correction. The second correction is calculated for the longitudinal relaxation values corresponding to the bins of the $T_2$ distribution. Correction B is then executed by multiplying each bin of the $T_2$ distribution by its correction B factor. The result is a T2 distribution where constant axial velocity artifacts and insufficient recovery time artifacts have been eliminated.

BRIEF DESCRIPTION OF THE DRAWINGS

The present invention is best understood with reference to the accompanying figures in which like numerals refer to like elements and in which.

DETAILED DESCRIPTION OF THE INVENTION

Figure 1:
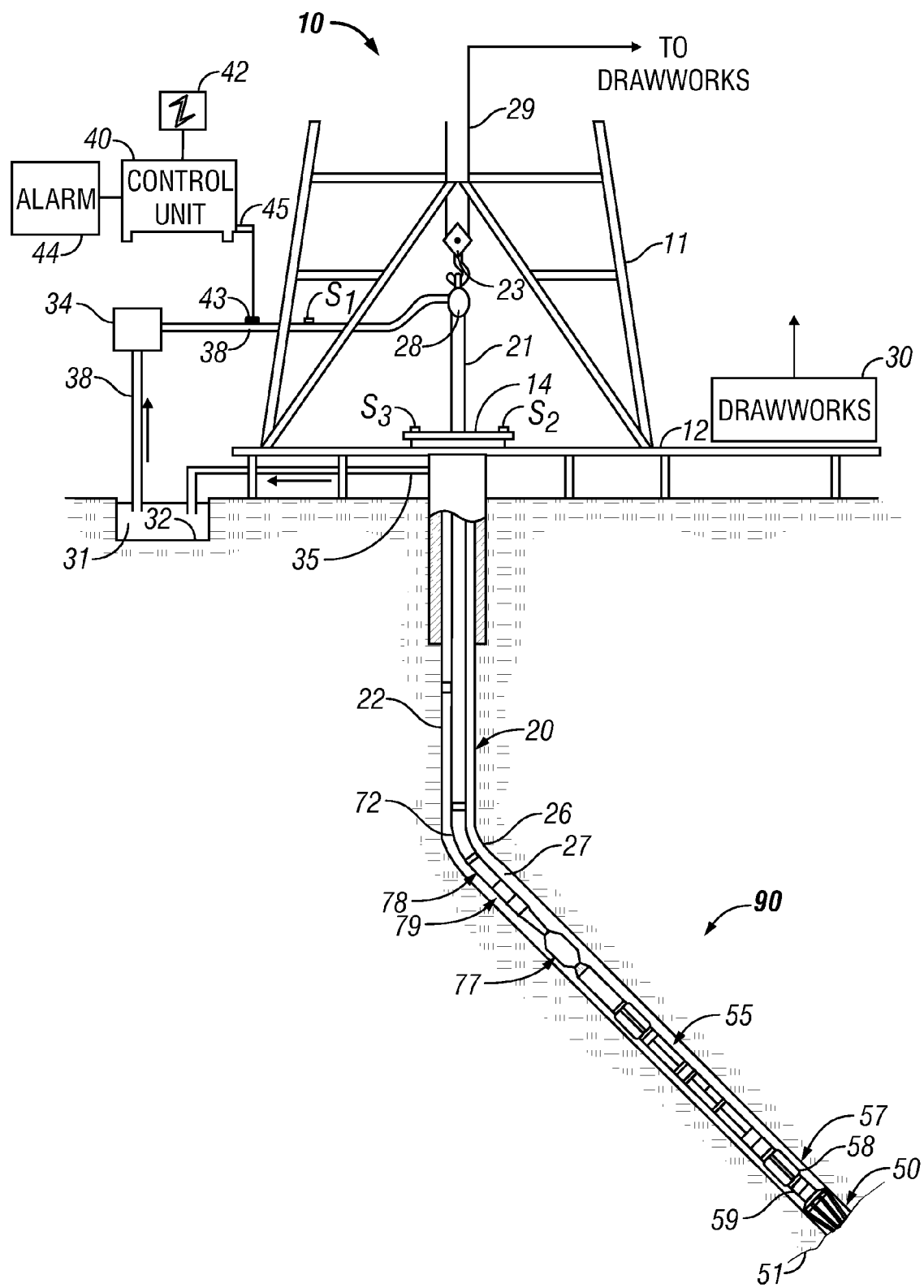
FIG. 1 shows a measurement-while-drilling tool suitable for use with the present invention.

FIG. 1 shows a schematic diagram of a drilling system 10 with a drillstring 20 carrying a drilling assembly 90 (also referred to as the bottom hole assembly, or "BHA" conveyed in a "wellbore" or "borehole" 26 for drilling the wellbore. The drilling system 10 includes a conventional derrick 11 erected on a floor 12 which supports a rotary table 14 that is rotated by a prime mover such as an electric motor (not shown) at a desired rotational speed. The drillstring 20 includes a tubing such as a drill pipe 22 or a coiled-tubing extending downward from the surface into the borehole 26. The drillstring 20 is pushed into the wellbore 26 when a drill pipe 22 is used as the tubing. For coiled-tubing applications, a tubing injector, such as an injector (not shown), however, is used to move the tubing from a source thereof, such as a reel (not shown), to the wellbore 26. The drill bit 50 attached to the end of the drillstring breaks up the geological formations when it is rotated to drill the borehole 26. If a drill pipe 22 is used, the drillstring 20 is coupled to a drawworks 30 via a Kelly joint 21, swivel 28, and line 29 through a pulley 23. During drilling operations, the drawworks 30 is operated to control the weight on bit, which is an important parameter that affects the rate of penetration. The operation of the drawworks is well known in the art and is thus not described in detail herein. For the purposes of this invention, it is necessary to know the axial velocity (rate of penetration or ROP) of the bottomhole assembly. Depth information and ROP may be communicated downhole from a surface location. Alternatively, the method disclosed in U.S. Pat. No. 6,769,497 to Dubinsky et al. having the same assignee as the present application and the contents of which are incorporated herein by reference may be used. The method of Dubinsky uses axial accelerometers to determine the ROP. During drilling operations, a suitable drilling fluid 31 from a mud pit (source) 32 is circulated under pressure through a channel in the drillstring 20 by a mud pump 34. The drilling fluid passes from the mud pump 34 into the drillstring 20 via a desurger (not shown), fluid line 38 and Kelly joint 21. The drilling fluid 31 is discharged at the borehole bottom 51 through an opening in the drill bit 50. The drilling fluid 31 circulates uphole through the annular space 27 between the drillstring 20 and the borehole 26 and returns to the mud pit 32 via a return line 35. The drilling fluid acts to lubricate the drill bit 50 and to carry borehole cutting or chips away from the drill bit 50. A sensor $S_1$ typically placed in the line 38 provides information about the fluid flow rate. A surface torque sensor $S_2$ and a sensor $S_3$ associated with the drillstring 20 respectively provide information about the torque and rotational speed of the drillstring. Additionally, a sensor (not shown) associated with line 29 is used to provide the hook load of the drillstring 20.

In one embodiment of the invention, the drill bit 50 is rotated by only rotating the drill pipe 22. In another embodiment of the invention, a downhole motor 55 (mud motor) is disposed in the drilling assembly 90 to rotate the drill bit 50 and the drill pipe 22 is rotated usually to supplement the rotational power, if required, and to effect changes in the drilling direction.

In an exemplary embodiment of FIG. 1, the mud motor 55 is coupled to the drill bit 50 via a drive shaft (not shown) disposed in a bearing assembly 57. The mud motor rotates the drill bit 50 when the drilling fluid 31 passes through the mud motor 55 under pressure. The bearing assembly 57 supports the radial and axial forces of the drill bit. A stabilizer 58 coupled to the bearing assembly 57 acts as a centralizer for the lowermost portion of the mud motor assembly.

In one embodiment of the invention, a drilling sensor module 59 is placed near the drill bit 50. The drilling sensor module contains sensors, circuitry and processing software and algorithms relating to the dynamic drilling parameters. Such parameters typically include bit bounce, stick-slip of the drilling assembly, backward rotation, torque, shocks, borehole and annulus pressure, acceleration measurements and other measurements of the drill bit condition. A suitable telemetry or communication sub 72 using, for example, two-way telemetry, is also provided as illustrated in the drilling assembly 90. The drilling sensor module processes the sensor information and transmits it to the surface control unit 40 via the telemetry system 72.

The communication sub 72, a power unit 78 and an MWD tool 79 are all connected in tandem with the drillstring 20. Flex subs, for example, are used in connecting the MWD tool 79 in the drilling assembly 90. Such subs and tools form the bottom hole drilling assembly 90 between the drillstring 20 and the drill bit 50. The drilling assembly 90 makes various measurements including the pulsed nuclear magnetic resonance measurements while the borehole 26 is being drilled. The communication sub 72 obtains the signals and measurements and transfers the signals, using two-way telemetry, for example, to be processed on the surface. Alternatively, the signals can be processed using a downhole processor in the drilling assembly 90.

The surface control unit or processor 40 also receives signals from other downhole sensors and devices and signals from sensors $S_1$-$S_3$ and other sensors used in the system 10 and processes such signals according to programmed instructions provided to the surface control unit 40. The surface control unit 40 displays desired drilling parameters and other information on a display/monitor 42 utilized by an operator to control the drilling operations. The surface control unit 40 typically includes a computer or a microprocessor-based processing system, memory for storing programs or models and data, a recorder for recording data, and other peripherals. The control unit 40 is typically adapted to activate alarms 44 when certain unsafe or undesirable operating conditions occur.

A suitable device for use of the present invention is disclosed in U.S. Pat. No. 6,215,304 to Slade, the contents of which are fully incorporated herein by reference. It should be noted that the device taught by Slade is for exemplary purposes only, and the method of the present invention may be used with many other NMR logging devices, and may be used for wireline as well as MWD applications. Examples of such devices are given in U.S. Pat. No. 5,557,201 to Kleinberg, U.S. Pat. No. 5,280,243 to Miller, U.S. Pat. No. 5,055,787 to Kleinberg, and U.S. Pat. No. 5,698,979 to Taicher.

Figure 2:
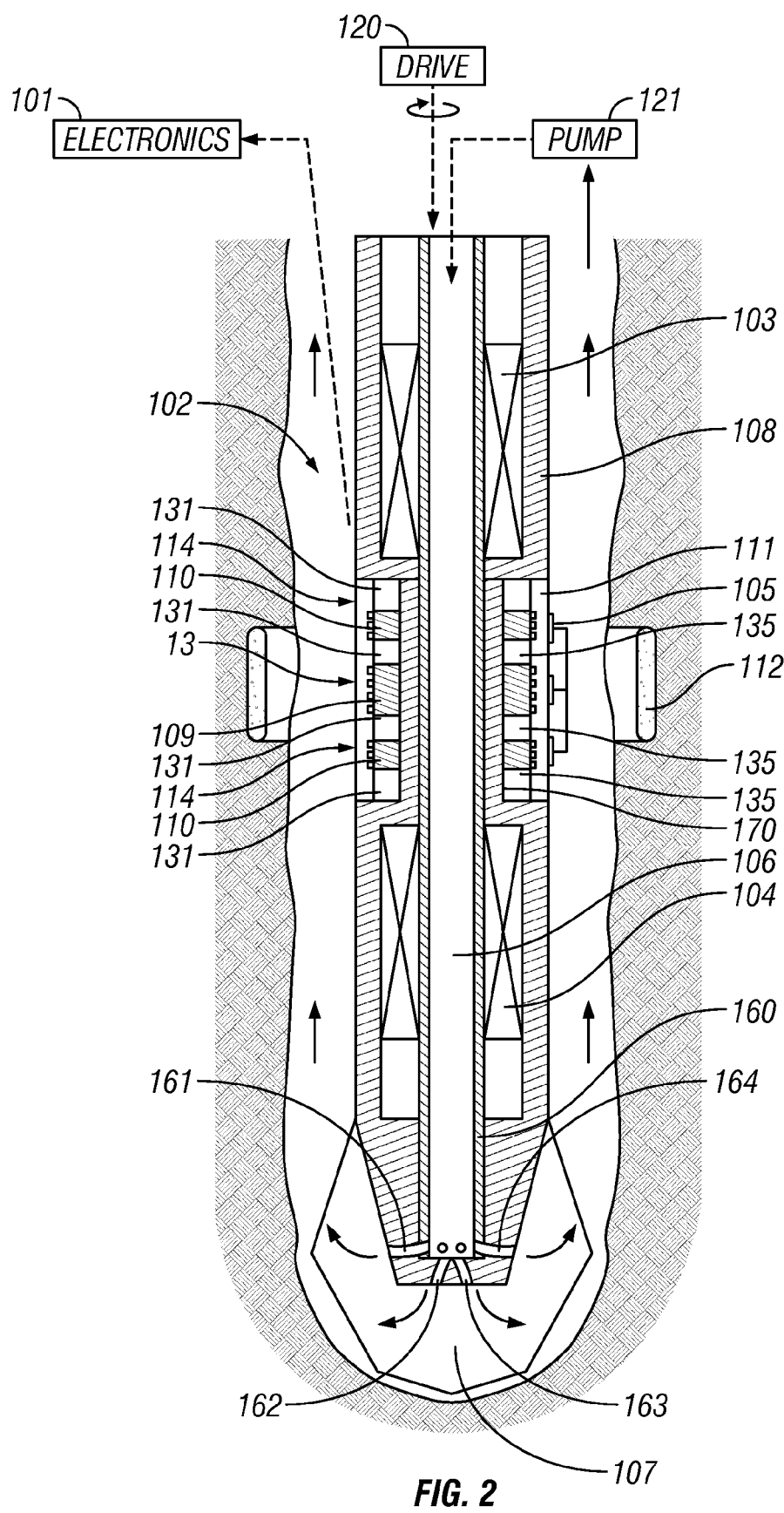
FIG. 2 shows a sensor section of a measurement-while-drilling device suitable for use with the present invention.

Referring now to FIG. 2, the tool has a drill bit 107 at one end, a sensor section 102 behind the drill head, and electronics 101. The sensor section 102 comprises a magnetic field generating assembly for generating a $B_0$ magnetic field (which is substantially time invariant over the duration of a measurement), and an RF system for transmitting and receiving RF magnetic pulses and echoes. The magnetic field generating assembly comprises a pair of axially spaced main magnets 103, 104 having opposed pole orientations (i.e. with like magnetic poles facing each other), and three ferrite members 109, 110 axially arranged between the magnets 103, 104. The ferrite members are made of "soft" ferrite which can be distinguished over "hard" ferrite by the shape of the BH curve which affects both intrinsic coercivity ($H_j$ the intersection with the H axis) and initial permeability ($\mu_i$, the gradient of the BH curve in the unmagnetized case). Soft ferrite $\mu_i$ values typically range from 10 to 10000 whereas hard ferrite has $\mu_i$, of about 1. Therefore the soft ferrite has large initial permeability (typically greater than 10, preferably greater than 1000). The RF system comprises a set of RF transmit antenna and RF receive antenna coil windings 105 arranged as a central "field forming" solenoid group 113 and a pair of outer "coupling control" solenoid groups 114.

The tool has a mud pipe 160 with a clear central bore 106 and a number of exit apertures 161-164 to carry drilling mud to the bit 107, and the main body of the tool is provided by a drill collar 108. Drilling mud is pumped down the mud pipe 160 by a pump 121 returning around the tool and the entire tool is rotated by a drive 120. Coiled tubing or a drillstring may be used for coupling the drive to the downhole assembly.

The drill collar 108 provides a recess 170 for RF transmit antenna and RF receive antenna coil windings 105. Gaps in the pockets between the soft ferrite members are filled with non-conducting material 131, 135 (e.g: ceramic or high temperature plastic) and the RF coils 113, 114 are then wound over the soft ferrite members 109, 110. The soft ferrites 109, 110 and RF coil assembly 113, 114 are pressure impregnated with suitable high temperature, low viscosity epoxy resin (not shown) to harden the system against the effects of vibration, seal against drilling fluid at well pressure, and reduce the possibility of magnetoacoustic oscillations. The RF coils 113, 114 are then covered with wear plates 111 typically ceramic or other durable non-conducting material to protect them from the rock chippings flowing upwards past the tool in the borehole mud.

Because of the opposed magnet configuration, the device of Slade has an axisymmetric magnetic field and region of investigation 112 that is unaffected by tool rotation. Use of the ferrite results in a region of investigation that is close to the borehole. This is not a major problem on a MWD tool because there is little invasion of the formation by borehole drilling fluids prior to the logging. The region of investigation is within a shell with a radial thickness of about 20 mm and an axial length of about 50 mm. The gradient within the region of investigation is less than 2.7 G/cm. It is to be noted that these values are for the Slade device and, as noted above, the method of the present invention may also be used with other suitable NMR devices.

Figure 3:
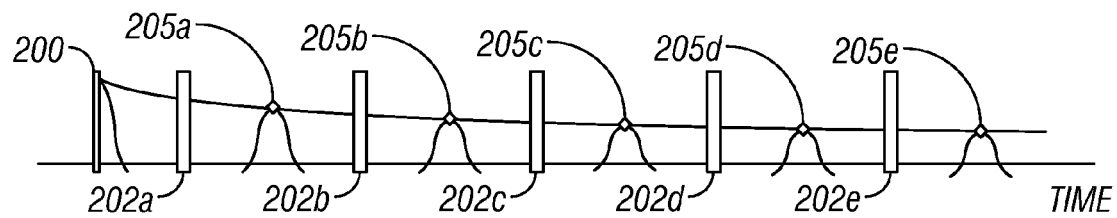
FIG. 3 shows a typical pulse sequence usable with the present invention.

Two magnetic fields are used to conduct a typical NMR measurement: a static magnetic field $B_0$ and an alternating magnetic field $B_1$, having a component orthogonal to $B_0$. Pulsed NMR is used in which the alternating field $B_1$, is radiated into the sample as a sequence of bursts (usually called pulses). A typical pulse sequence is shown in FIG. 3. The $B_1$, pulse sequence comprises an excitation pulse 200 followed by a plurality of refocusing pulses (202a, 202b, 202c, 202d, 202e, . . . ). Spin echoes depicted by 205a, 205b, 205c, 205d, 205e, . . . form between these refocusing pulses. These echoes manifest themselves as rotating macroscopic magnetizations and can be detected with a receiver coil. The induced voltages/currents in this coil are the desired NMR signals. In order to obtain NMR signals and refocus them correctly, it is important to adhere to NMR resonance conditions, i.e. $B_0$ and $B_1$ amplitudes as well as pulse phases and shapes need to be chosen correctly as known to people familiar with the art of NMR (see Fukushima, *Experimental Pulse NMR: A Nuts and Bolts Approach*, 1981, Tenth printing, January 1998.). An exemplary optimized echo sequence called ORPS is discus in Hawkes '013. In the ORPS sequence, the tipping pulse is typically 90°, but the refocusing pulses are less than 180°. This is in contrast to the CPMG sequence in which the refocusing pulses are 180° pulses.

Generally, the geometry of the NMR measurement device gives rise to a volume in the earth formation where the $B_0$ field has the correct strength to fulfill a resonance condition and in which an RF field can be presented with a substantial strength and orientation to reorient nuclear spins within the volume. This volume is often referred to as the sensitive volume. For a tool in motion, as the tool moves axially, the volume containing those protons excited by the excitation pulse (first pulse of the echo sequence) moves away from the sensitive volume. Hence, the number of spins available to contribute to the subsequent NMR signal is reduced with each subsequent echo. As a consequence, those echoes obtained later in an echo sequence with axial tool motion appear small compared to those echoes obtained later in an echo sequence acquired with no tool motion. "Later echoes" does not mean that only the last echoes of a sequence are affected. In fact, the loss of signal starts right at the beginning of a sequence and develops over time in a unique pattern.

The magnet configuration of FIG. 2 produces a somewhat inhomogeneous static magnetic $B_0$ field. Measured in the axial direction, this field has a minimum at the center of the NMR sensor and increases in magnitude to a maximum at the magnets. The result of this configuration on a volume of formation being traversed in an axial direction is that during constant axial motion the formation first comes close to one of the magnets and is magnetized by this higher field. As the NMR sensor center moves closer, the effective $B_0$ field decreases. But the formation "remembers" the earlier higher magnetization and only gradually decays, with the time constant $T_1$, towards the minimum equilibrium magnetization $B_0$ field located in the center.

In general, NMR echo sequences are repeated several times for the purpose of increasing the final signal-to-noise ratio. Even without concern over signal-to-noise ratio, an echo sequence is usually repeated at least once in order to form a phase-alternated pair (PAP) for the purpose of removing offset and ringing effects.

At the end of a sequence obtained with axial tool motion, the magnetization of the sensitive volume is substantially zero. A wait time during which re-magnetization of the formation occurs is used as part of the sequence of pulses. Choosing a wait time of at least 5 times the longest $T_1$ of the formation ensures that the formation is fully magnetized (>99% magnetization) immediately prior to the excitation pulse of the ensuing sequence. However, shorter wait times are often chosen in order to achieve a higher NMR data rate, leading to an improved axial resolution or signal-to-noise ratio. The drawback of shortening TW is that the formation may not be fully magnetized immediately prior to the ensuing sequence. As a consequence, the total porosity that is measured in a tool having axial motion can be too low, and the measured $T_2$-distribution is generally distorted, mainly for the longer $T_2$ components.

The method of the present invention corrects for artifacts that result from axial motion and from a shortened wait time (TW) between consecutive pulse sequences. The correction of the spin echo decay (and hence $T_2$ distribution) for axial motion is referred to herein as Correction A and the correction for pre-magnetization and shortened TW is referred to herein as Correction B.

The simulations of FIGS. 4-8 are obtained using an NMR simulation for a tool such as that shown in FIG. 2. For these simulations, the duration of the applied excitation pulse is 50 μs, and the duration of the applied refocusing pulses is 70 μs. Such a pulse sequence has been described in U.S. Pat. No. 6,466,013 to Hawkes et al., having the same assignee as the present application and the contents of which are incorporated herein by reference. It may be referred to in the present document as the Optimized Rephasing Pulse Sequence (ORPS). For the simulation, a pulse amplitude of 40 A is used. The sensitive volume is substantially located within radial distances r=130 mm to r=230 mm and within axial distances z=−70 mm to z=70 mm. A 2-dimensional simulation is used.

Figure 4:
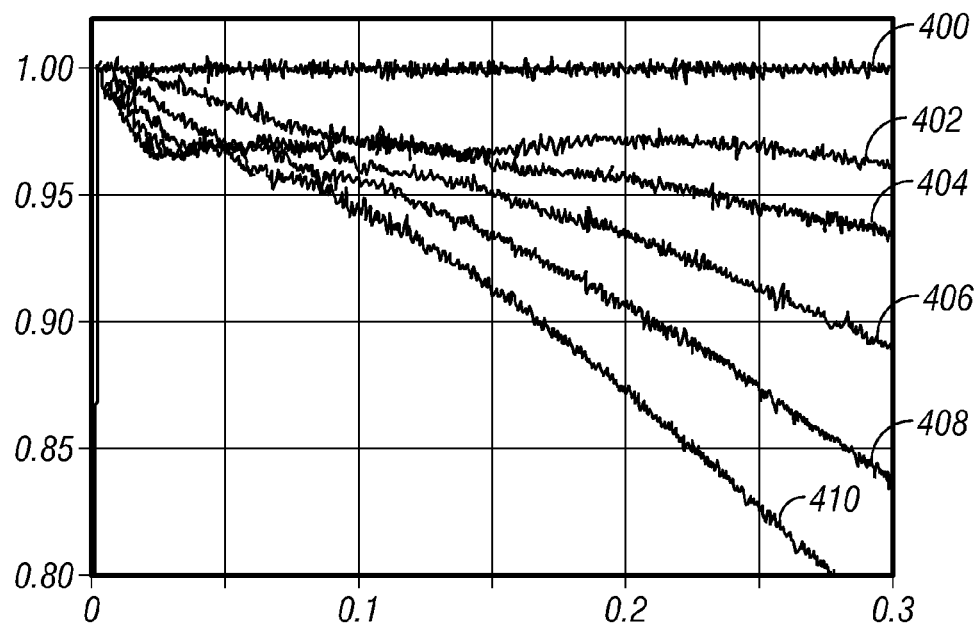
FIG. 4 shows six NMR spin echo decay curves obtained at varying axial motions of a drillstring through a formation.

FIG. 4 shows six echo trains obtained at various axial velocities of a drillstring through a formation. The six echo trains are obtained at different velocities: (402), (404), (406), (408), (410) with increasing velocity, (400) with zero velocity. Time is measured along the horizontal axis and normalized NMR signal magnitude along the vertical axis. 1000 echoes are used in the pulse sequence with TE=0.6 ms. Significantly, the curves obtained at the smaller non-zero velocities (402, 404, 406, and 408) can all be derived from the curve obtained for the highest velocity (410) by simply compressing the horizontal axis.

Figure 5:
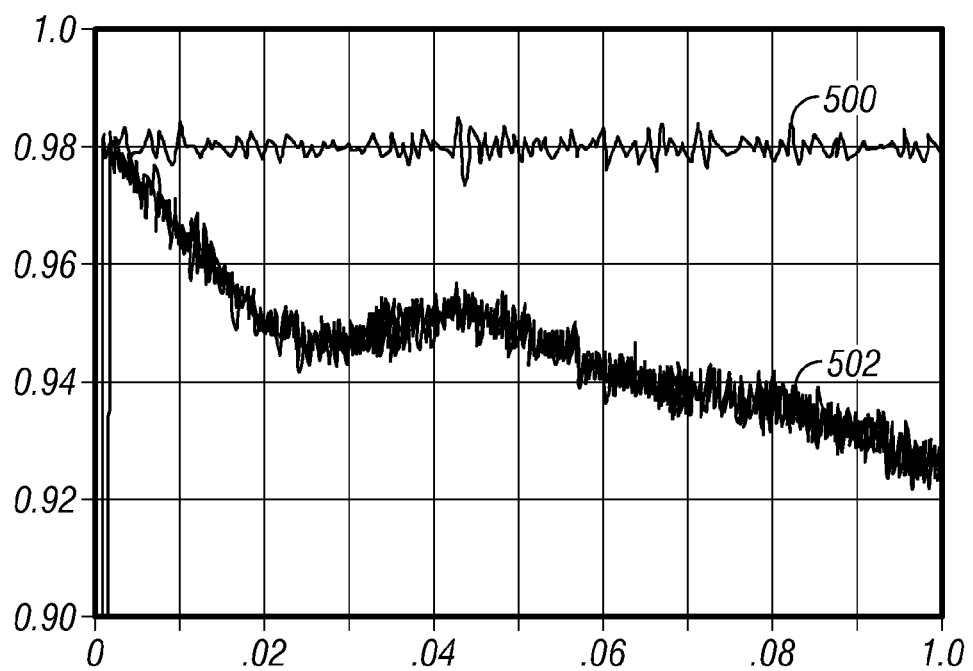
FIG. 5 shows the results of a compression of the horizontal axis of FIG. 4.

The results of this compression of the horizontal axis is shown in FIG. 5. The echo decay curves obtained with axial motion (402, 404, 406, 408, and 410 in FIG. 4) fall now nearly on top of each other, as indicated by the curve 502. The curve 500 indicates a signal obtained with no axial tool motion. This alignment of "compressed" echo decays indicates that the echo amplitudes are not velocity-dependent, but only position-dependent. In other words, there is no significant phase error due to the magnitude of the axial motion. This finding is consistent with the fact (not shown) that there is no significant change in the imaginary part of the NMR signal when comparing zero velocity and the highest velocity.

A first correction, referred to hereafter as Correction A is discussed next. This correction is intended to address the effects of axial tool motion. The curves of FIG. 4 can be fitted to a mathematical function. Due to the characteristic shape at the start of the echo sequence, a simple polynomial does not work well. However, a perturbing term can be introduced to characterize the fluctuation at small times. An exemplary function including a damped cosine term as the perturbing term is employed for the example of Eq. (3).

$$fcA(t) = P_0 + P_1 \cdot t + P_2 \cdot t^2 + P_3 \cdot t^3 + P_4 \cdot t^4 + P_5 \cdot t^5 + P_6 \cdot t^6 + P_7 e^{-P_8 \cdot t} \cdot \cos(P_9 \cdot t) \quad (3).$$

Eq. (3) adequately fits the echo decay curve with the highest velocity (410 of FIG. 4). P-parameters can be obtained through a fitting method to the raw data.

It should be noted, that the equation strongly depends on the geometric shape of the sensitive area, where the measurement is carried out. The use of a damped cosine in Eq. (3) is not meant as a limitation of the present invention, and any function appropriate for this mathematical description can be used.

Assuming an array of NMR echo amplitudes A(t) and of axial velocity $V_{axial}$, one can calculate the corrected amplitude $A_{cor}(t)$ using the formula shown in Eq. (4) below:

$$A_{cor}(t) = \frac{A(t)}{f_c\left(t \cdot \frac{V_{axial}}{V_{ref}}\right)} \quad (4)$$

where $fc$ is the function expressed in Eq. (3) with the parameter set given there. This correction can be used for any NMR channel, i.e., independently, real and imaginary (or in-phase and quadrature).

Figure 6:
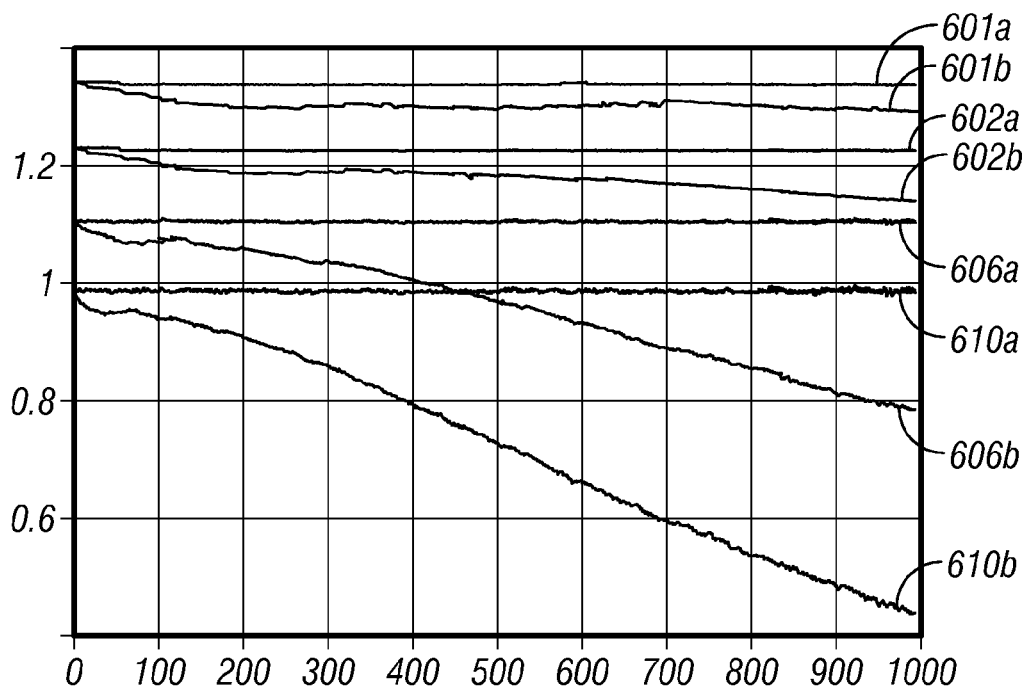
FIG. 6 shows simulations obtained with an infinite $T_2$ in the simulation.

FIG. 6 shows simulations obtained assuming an infinite $T_2$ decay. Raw traces from the simulations obtained at different axial velocities are shown. For convenience, the different axial velocities will be termed as low velocity, medium velocity, medium high velocity, and high velocity, In FIG. 6, these are shown by 601b, 602b, 606b, and 610b respectively The traces which result after applying Correction A for axial velocity are labeled (601a), (602a), (606a), and (610a). The horizontal axis displays the number of echoes, while the vertical axis displays normalized amplitude. In order to better differentiate the individual curves vertical offsets are applied to the curves 601a/b, 602a/b and 606a/b. Ideally, the corrected echo traces should be straight lines. As FIG. 6 shows, the corrected traces substantially approach the ideal.

Figure 7:
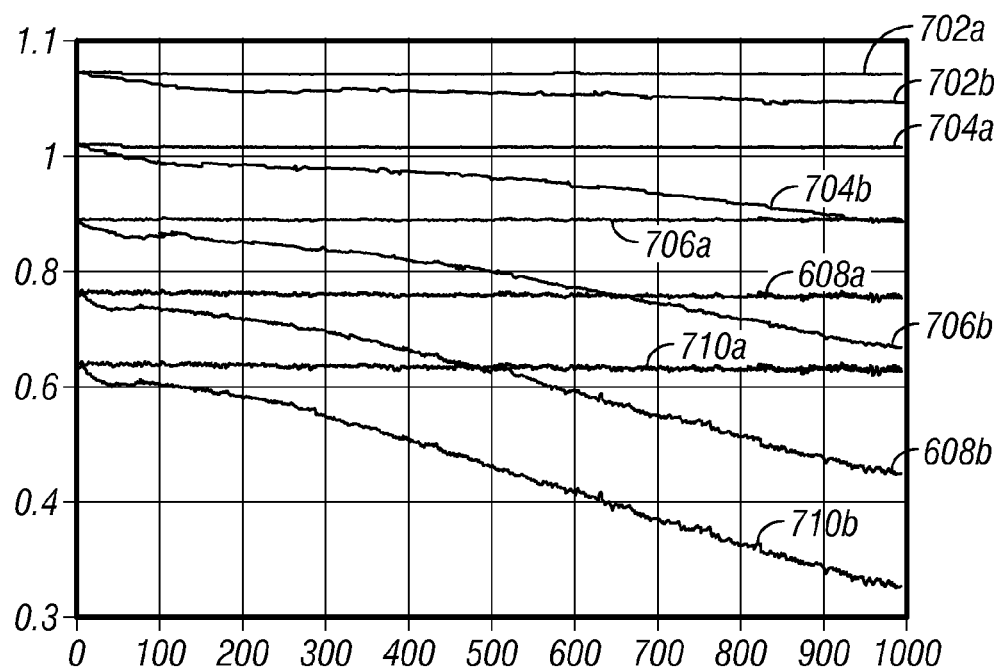
FIG. 7 shows simulations using an RF current amplitude different from that used in FIG. 6.

Variations in the shapes of RF pulses affect the corresponding artifacts. The exact shape of the motion artifact depends on the type of RF pulse sequence used. FIG. 7 shows simulations using a different RF current amplitude. Raw traces from the simulations were performed at the different axial velocities from above. Low velocity (702b), medium low (704b), medium (706b), medium high (708b), and high velocity (710b) are shown. The traces which result after applying Correction A for axial velocity are labeled for (702a), (704a), (706a), (708a), and (710a). The horizontal axis displays the number of echoes, while the vertical axis displays normalized amplitude. In order to better differentiate the individual curves vertical offsets are applied to the curves. There are 1000 echoes shown with inter-echo spacing TE=0.6 ms. Through comparison of FIG. 7 to results shown in FIG. 6 for the higher RF-pulse amplitude (on which the correction function is based), Correction A proves to be robust under variations of the RF pulse.

Alternately, varying the ratio of RF pulse areas between the excitation pulse and refocusing pulses leads to various artifacts. For instance, for a sequence with a selective excitation pulse, the signal reduction at the beginning of the sequence can be avoided. A correction function can be chosen so as to enable correction of a trace resulting from the selective excitation pulse sequence. Alternatively, a different fit function can be chosen for different RF pulse sequences or different echo integrations, such as disclosed in U.S. U.S. patent application Ser. No. 10/839,478 of Blanz et al.

Figure 8:
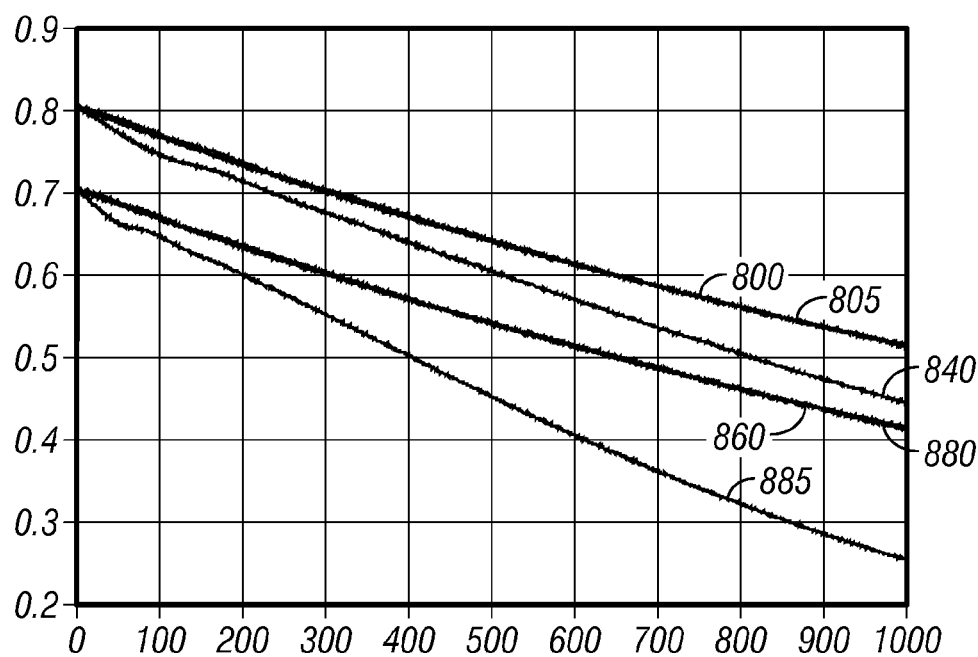
FIG. 8 shows the effect of applying a correction function of the present invention for a simulation with finite $T_2$.

FIG. 8 shows that the correction function of Eq. (1) obtained using a simulation with infinite $T_2$ can be used for real NMR signals having finite $T_2$. A thousand echoes are shown along the horizontal axis at an interecho spacing of TE=0.6 ms. The vertical axis shows NMR amplitudes but with vertical offsets to differentiate the curves on the graph. Corrections are made on curves 840 and 885. Simulations are performed using a finite $T_2$ ($T_2$=1 sec) and different velocities for (840) and (885). Three echo decays are shown for each velocity: the uncorrected decay, the corrected decay, and the zero velocity decay. For example, in FIG. 8 uncorrected decay 840 is corrected to obtain corrected decay 805, which is compared with zero velocity decay 800. Similarly, uncorrected decay 885 is corrected to obtain corrected decay 880, which is compared with zero velocity decay 860.

Figure 9:
FIG. 9 shows 2 ORPS sequences separated by a wait time TW.

Another correction, referred to as Correction B, that may be applied in the present invention to correct for effects of excessive pre-magnetization and reduced TW, is discussed next. FIG. 9 shows 2 ORPS sequences only separated by a wait time TW. Both ORPS have 1000 echoes each, TE=0.6 s. The wait time TW is 1 s.

Figure 10:
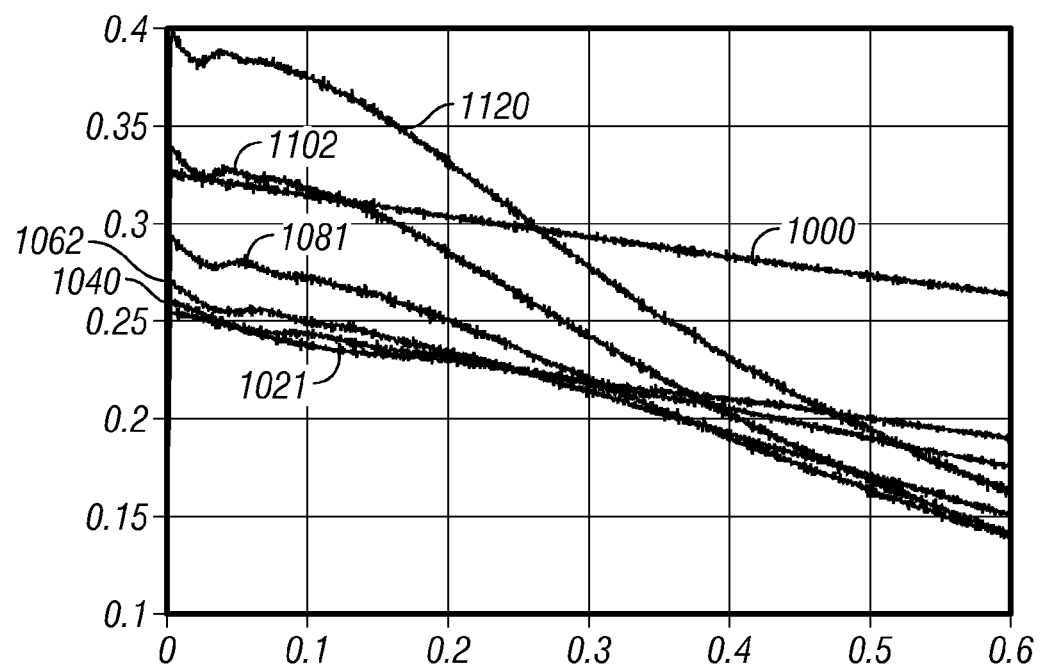
FIG. 10 shows a simulation example of echo decays produced using the second ORPS sequence from FIG. 9.

When the wait time between ORPS sequences is shorter than five times the longest $T_1$ in the earth formation, the latter sequence begins before proper magnetization has been achieved. Therefore, the amplitude of the resultant NMR signal depends on the degree of remnant magnetization after the previous sequence and on the duration of the wait time. The magnetization after an ORPS sequence applied with axial tool motion is substantially zero. However, if there is no motion during the first ORPS, an appreciable amount of z-magnetization is left. FIG. 10 shows simulation examples of echo decays produced using the second ORPS sequence from FIG. 9. For the simulation of FIG. 10, $T_1$=$T_2$=2.5 sec. Simulations are made at zero velocity (1000), low axial velocity (1021), increasing axial velocities (1040), (1062), (1081), (1102) and highest velocity (1120). Excessive pre-magnetization effects due to moving formation material, which has been exposed to a higher magnetic field in the close vicinity of the magnets, can be seen. In this case the initial magnitudes (at t=0) of the decay traces of FIG. 10 increase with increasing velocity—with one exception. An exception is found in the trace of zero velocity, which has an initial amplitude higher than the initial amplitudes obtained at higher velocities. This exception is high due to z-magnetization left after the end of the first ORPS, which is due to the periodic nature of ORPS. Axial velocity disturbs this coherence effect.

Figure 11:
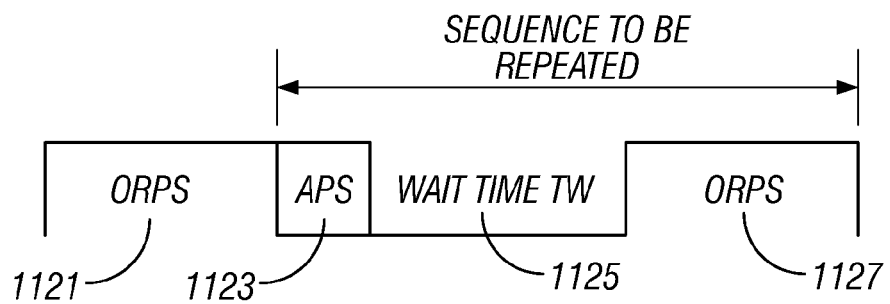
FIG. 11 shows the use of an aperiodic pulse sequence (APS)

In order to counteract the anomalous initial amplitude found at zero velocity, a shortened saturation sequence can be applied. An exemplary shortened saturation sequence is an aperiodic pulse sequence (APS) such as shown in FIG. 11.

In an exemplary mode of the present invention, an APS is constructed with eight saturation pulses (e.g. of 50 μs length) with reducing interpulse times 6400 μs, 3200 μs, 1600 μs, 800 μs, 400 μs, 200 μs, 100 μs. The corresponding phases are 0°, 180°, 90°270°, 0°, 180°, 90°, and 270°. The total duration of this sequence is 12.7 ms+8*50 μs=13.1

For reliable pre-magnetization correction (B) a short aperiodic saturation sequence as described herein is preferable, not only for the simulation but also in the real NMR logging run. As an eight-pulse APS is only 13 ms long, there is no disadvantage in doing this. This is shown in FIG. 11 by the initial ORPS (or CPMG sequence) 1121, the APS sequence 1125, the wait time 1125, and a repeat of the ORPS 1127.

Figure 12:
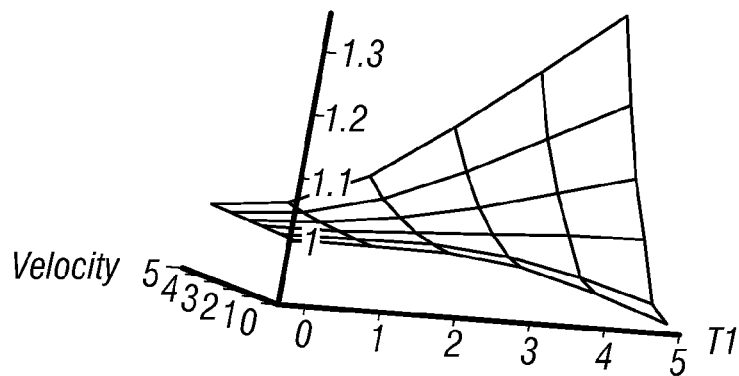
FIG. 12 shows the effect of hyperpolarization and insufficient wait time.

FIG. 12 shows results of simulations to obtain corrections for excessive pre-polarization and long $T_1$ (with insufficient wait time). These simulations employ an APS and have the following properties: the first ORPS has 1000 pulses with TE=0.6 ms; TW =6 sec; and the second ORPS has only two refocusing pulses and produces two echoes of which the second echo is used for determination of the echo amplitude. Therefore FIG. 12 does not show a discontinuity towards zero velocity.

The magnitude of the echo amplitude obtained using the pulse sequence of FIG. 11 depends on the two variables, axial velocity (v), and $T_1$. Analysis using discrete values of $T_1$ can be performed. In an example of a complete analysis, 6 discrete velocities and 6 discrete values of $T_1$ are chosen and a simulation is run for each combination of these. This gives rise to a matrix of normalized echo amplitudes $S_n$ such as shown in the matrix of Eq. (5).

$$S_n = \begin{bmatrix} 1 & S_{12} & \cdots & S_{1M} \\ 1 & S_{22} & \cdots & S_{2M} \\ \vdots & \vdots & \ddots & \vdots \\ 1 & S_{N2} & \cdots & S_{NM} \end{bmatrix} \quad (5)$$

From left to right in matrix $S_n$, $T_1$ increases from zero to a maximum value. From top to bottom, the axial velocity increases from zero to a maximum value. A graphical 3-dimensional representation of matrix $S_n$ is shown in FIG. 12.

The simulated echo amplitudes of matrix Sn can be fitted to an analytical function. In one embodiment of the invention the fitting function is a polynomial of the form $$p(v,t) := \sum_{i=0}^{last\ (coeffs)} coeffs_i \cdot v^{I_{i,0}} \cdot t^{I_{i,1}} \quad (6)$$

where v is the axial velocity and t the spin-lattice relaxation time $T_1$ with the exponents taken from the Table 1 below.

TABLE 1

| I | $I_{i,0}$ | $I_{i,1}$ |
|---|---|---|
| 0 | 1 | 2 |
| 1 | 0 | 3 |
| 2 | 0 | 2 |
| 3 | 0 | 1 |
| 4 | 1 | 1 |
| 5 | 2 | 1 |

TABLE 1-continued

| I | $I_{i,0}$ | $I_{i,1}$ |
|---|---|---|
| 6 | 0 | 0 |
| 7 | 1 | 0 |
| 8 | 2 | 0 |
| 9 | 3 | 0 |

Because the fit function necessarily depends on two variables, a multivariate regression can be used. Eqs. (7) below shows fit matrix $S_{fit}$ and the form of the error matrix (using a polynomial of the third order).

$$S_{fit} = \begin{bmatrix} S_{f11} & S_{f12} & \cdots & S_{f1M} \\ S_{f21} & S_{f22} & \cdots & S_{f2M} \\ \vdots & \vdots & \ddots & \vdots \\ S_{fN1} & S_{fN2} & \cdots & S_{fNM} \end{bmatrix} \quad (7)$$

$$100 \cdot (S_{fi} - S_n) = \begin{bmatrix} S_{e11} & S_{e12} & \cdots & S_{e1M} \\ S_{e12} & S_{e22} & \cdots & S_{e2M} \\ \vdots & \vdots & \ddots & \vdots \\ S_{eN1} & S_{eN2} & \cdots & S_{eNM} \end{bmatrix}$$

Figure 13:
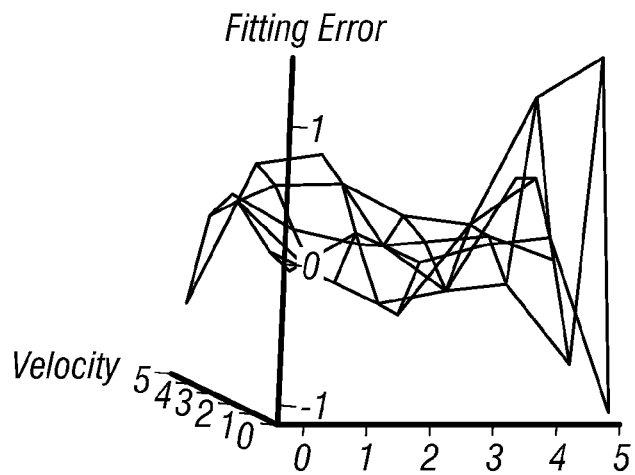
FIG. 13 shows the error of fitted correction B.

FIG. 13 shows the percentage error between the fit and simulated data $(S_{fit}-S_n)*100$. An improved fit can be obtained through use of a higher-order polynomial in exchange for the inconvenience of an increase in the number of coefficients.

Along with axial velocity (v) and $T_1$, a third parameter, TW, can also be varied, and a polynomial of three variables, p(v, T1,TW), can be fitted to the resultant curve. The two-dimensional matrix of equation 5 and FIG. 12 then becomes a 3-dimensional matrix, with the third dimension being the variable TW. The power of exponents (Table 3) will then have three columns instead of two. For the same order polynomial (here third order), there will be more coefficients. For a third dimension, there are 20 coefficients, while for two dimensions there are only 10 coefficients. Rather than plotting one graph, equivalent to FIGS. 12-13, several graphs can be plotted for individual TWs.

To apply correction B (to correct for artifacts due to pre-magnetisation and shortened TW), one can divide the echo decay amplitudes (preferably after having applied correction A) by the scalar resulting from evaluation of the polynomial outlined in Eq. (6). The axial velocity (v) and $T_1$ of the NMR sample are recorded prior to this correction.

Correction B can be used with any echo decay sequence. The success of this method of using Correction B is due to the fact that Correction B only corrects the magnetization at the beginning of the echo sequence. This initial magnetization depends on the (magnetic) geometry of the NMR logging tool, the axial velocity (v) during the wait time TW, and T1.

Correction B is an approximation for low axial velocities. At high axial velocities, the z-magnetization is affected by relaxing pre-magnetization also within the ORPS sequence. Including the effects of high axial velocity in the pre-magnetization involves increasing the dimension of the polynomial by 1, i.e. the use of a polynomial of 3 or 4 variables.

Figure 14:
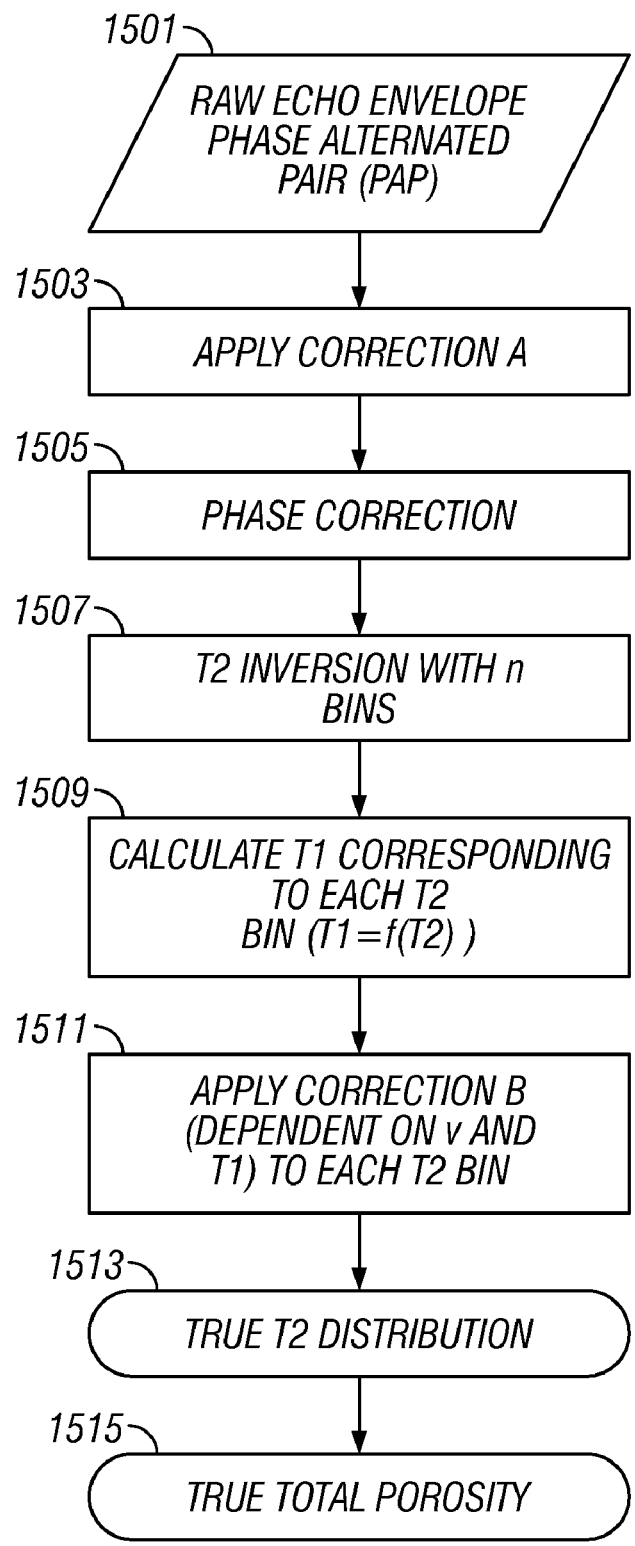
FIG. 14 shows a flowchart of the present invention in the presence of a $T_1$ distribution.

FIG. 14 shows a flowchart of the present invention in the presence of a $T_1$ distribution. In a real earth formation, a $T_1$ distribution (rather than a single $T_1$ value) should be expected. Also a $T_2$ distribution is expected. After $T_2$ inversion of the echo envelope data (after having applied correction A), each $T_2$ bin represents a single exponential decay function with a characteristic $T_2$ and the weight given by the height of the bin. The superposition of all these exponential functions constitutes a multi-exponential fit to the original decay data. Because of the linear addition of individual exponential decays, Correction B can be applied to each exponential separately, i.e. applying Correction B to each bin of the $T_2$ distribution, where all bins have a common axial velocity but individual $T_1$. For the case of $T_1=f(T_2)$ where the function $f(T_2)$ is known, the required $T_1$ can be obtained directly from the distribution of $T_2$. For example, the relationship between $T_1$ and $T_2$ might be simply a factor $T_1=fac*T_2$ were "fac" would normally be in the range of 1 to 2. Making use of this relationship enables one to attribute a specific $T_1$ to each bin of the $T_2$ distribution. Correction B can therefore be applied in the form of a height correction factor individually to each bin to arrive finally at the true $T_2$ distribution, where "true" means that all artifacts due to (constant) axial velocity and insufficient wait time are corrected.

In Box 1501 of FIG. 14 the raw data is obtained, typically using a phase alternated pair sequence. Correction A (correction for axial velocity) is applied in Box 1503. Any desired phase correction that is needed can be applied in Box 1505. A $T_2$ inversion can be obtained having n bins (Box 1507). As $T_1$ is functionally dependent on $T_2$, the $T_1$ corresponding to each $T_2$ is consequently calculated in Box 1509. Correction B (correction dependent on axial velocity and $T_1$) is applied to each $T_2$ bin in Box 1511. The correction B is applied to this decaying exponential. From the application of correction B, a corrected $T_2$ is obtained for each bin, and thence for the entire $T_2$ distribution (Box 1513). The result of the calculations leads to improved results for true total porosity (Box 1515).

Figure 15:
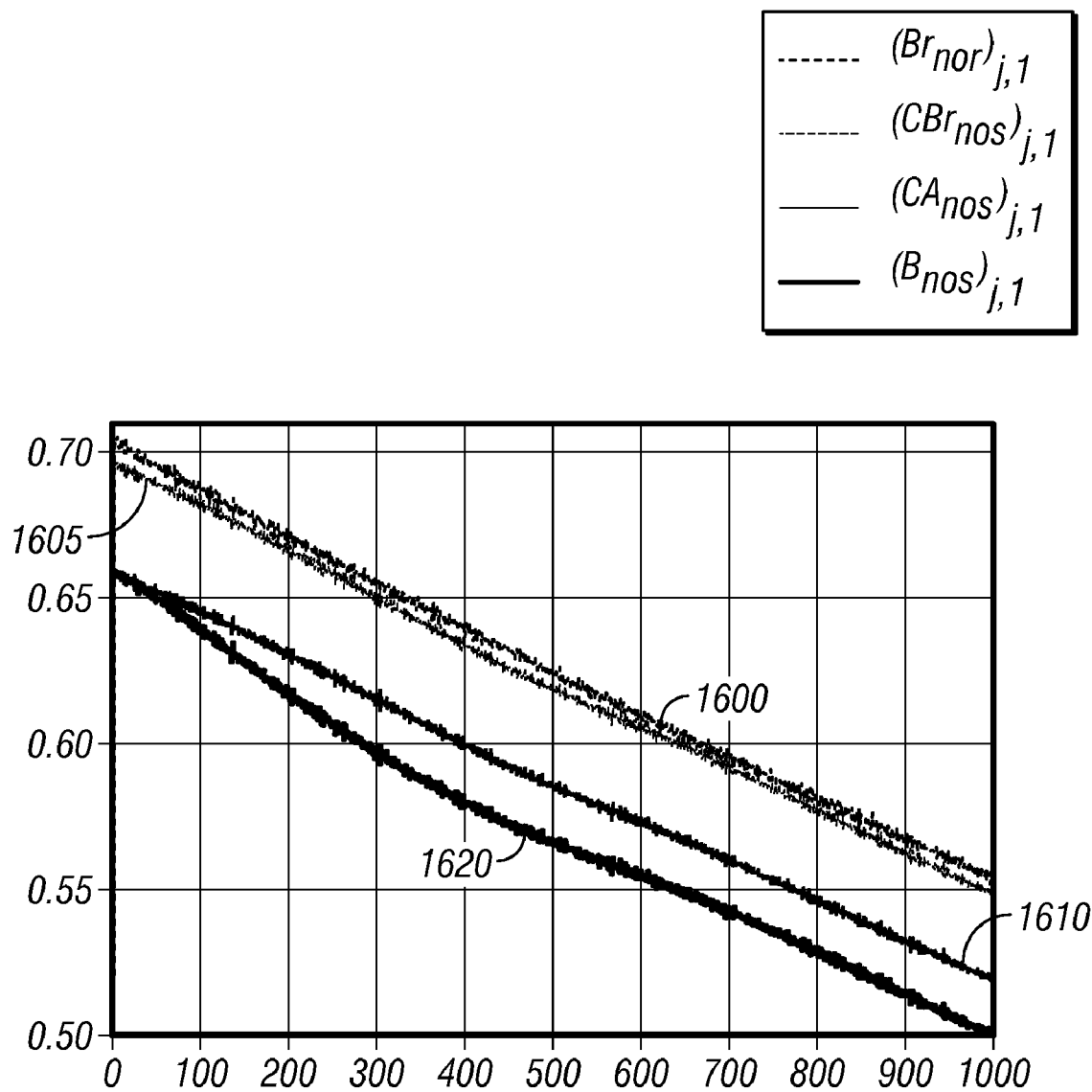
FIG. 15 shows a simulation of NMR data with the use of an APS sequence (FIG. 11) and applied corrections A and B.

FIG. 15 shows a simulation of NMR data using the APS sequence of FIG. 11. A simulation is performed for a low drilling speed and $T_1=2.2$ msec to test the corrections A and B for an exemplary case. Trace 1600 is the reference echo decay trace obtained with full equilibrium magnetization and zero velocity. Trace 1620 is an uncorrected echo decay trace. Trace 1610 is the trace resulting after correction A is applied to trace 1620, and trace 1605 is the trace resulting after correction A and B are applied. This data is not normalized. The corrected trace 1605 is about 1% lower than the reference trace 1600. The percentage error just stated for FIG. 15 is a relative error. At a total porosity of (e.g.) true 20%, a relative error of −1% would lead to a result that is by 1% (relative) too small, i.e., this porosity would be plotted as 20%*0.99=19.8%.

Pulse sequences or echo processing methods that are a priori less sensitive to motion than standard pulse sequences can be used with the present invention. Some such methods have been disclosed in U.S. patent application Ser. No. 10/839,478 of Blanz et al. Such pulse sequences are easy to use (at the penalty of some loss of signal-to-noise ratio). Methods to reduce the sensitivity to irregular small amplitude motion (vibration) can be combined with the corrections A and B for ROP correction as described in this document. Correction A will depend on this other motion artifact reduction method and must be tailored accordingly.

The methods discussed above use measurements or estimates of the downhole axial velocity for applying corrections to individual NMR echo sequences. An alternate embodiment of the invention uses an average axial velocity for applying the correction. The average velocity may be estimates using surface depth measurements that are typically obtained every 30 s or so in normal drilling operations. The use of average velocities is illustrated using simulations of the type discussed above.

NMR echo trains were simulated with ORPS sequence for the following exemplary axial velocities: 20 m/h, 40 m/h, 60 m/h, 80 m/h, 100 m/h, 120 m/h and 140 m/h. 5 to 7 of these simulations were averaged to result in an averaged NMR echo sequence and in an averaged velocity. These examples are (numbers indicating velocity in m/h):

60, 80, 100, 120, 140→average 100;

60, 80, 100, 100, 140→average 96;

60, 60, 80, 80, 120, 140→average 90;

60, 80, 80, 80, 120→average 84;

40, 60, 60, 100, 120→average 76:

20, 40, 60, 60, 80, 80, 120→average 66;

20, 40, 40, 60, 80, 100→average 57;

20, 40, 40, 40, 80, 100→average 53;

20, 20, 40, 40, 60, 100→average 47;

20, 20, 20, 40, 40, 60, 100→average 43.

Figure 16:
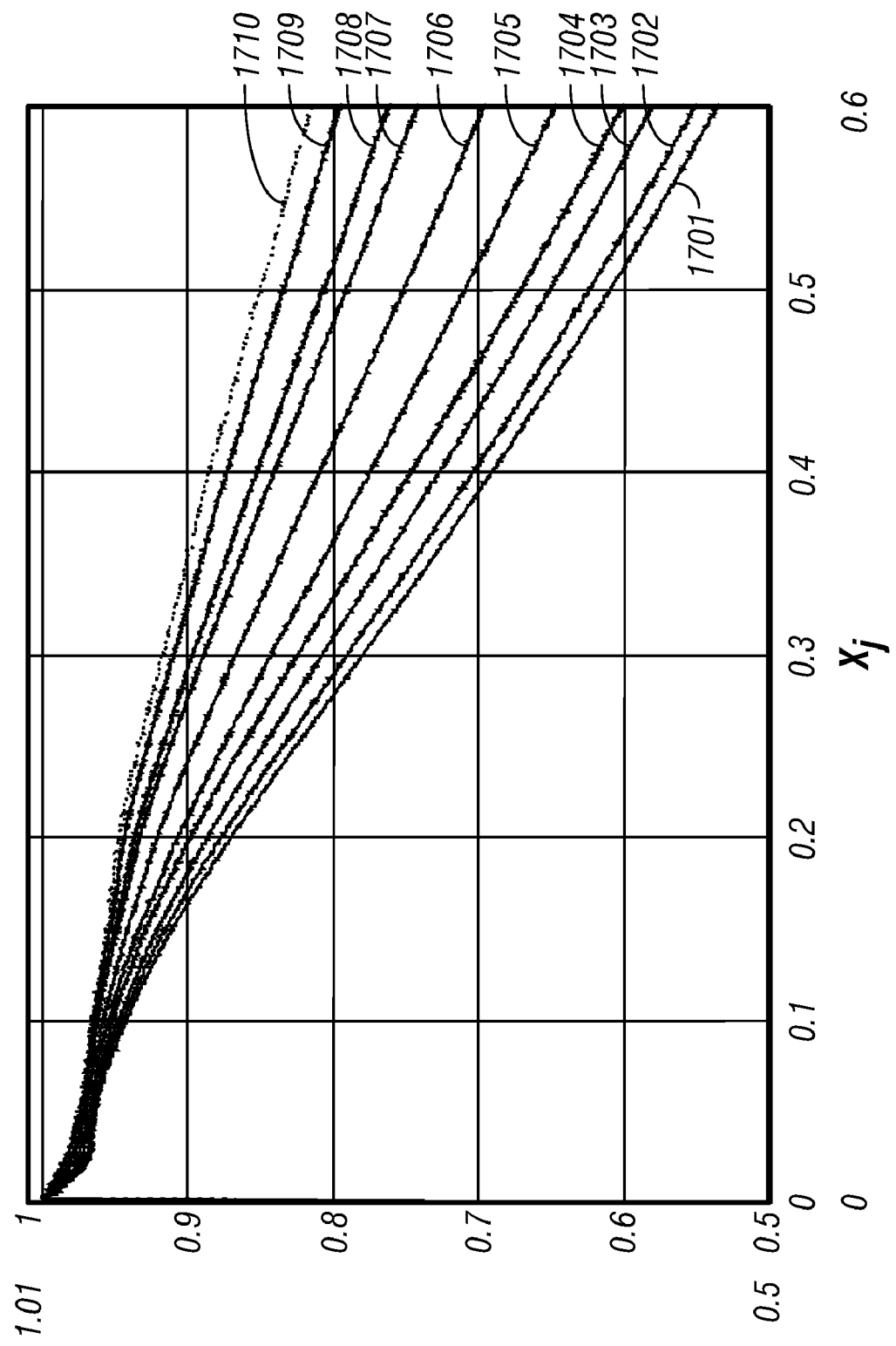
FIG. 16 shows simulated echo amplitudes of averaged echo trains.
Figure 17:
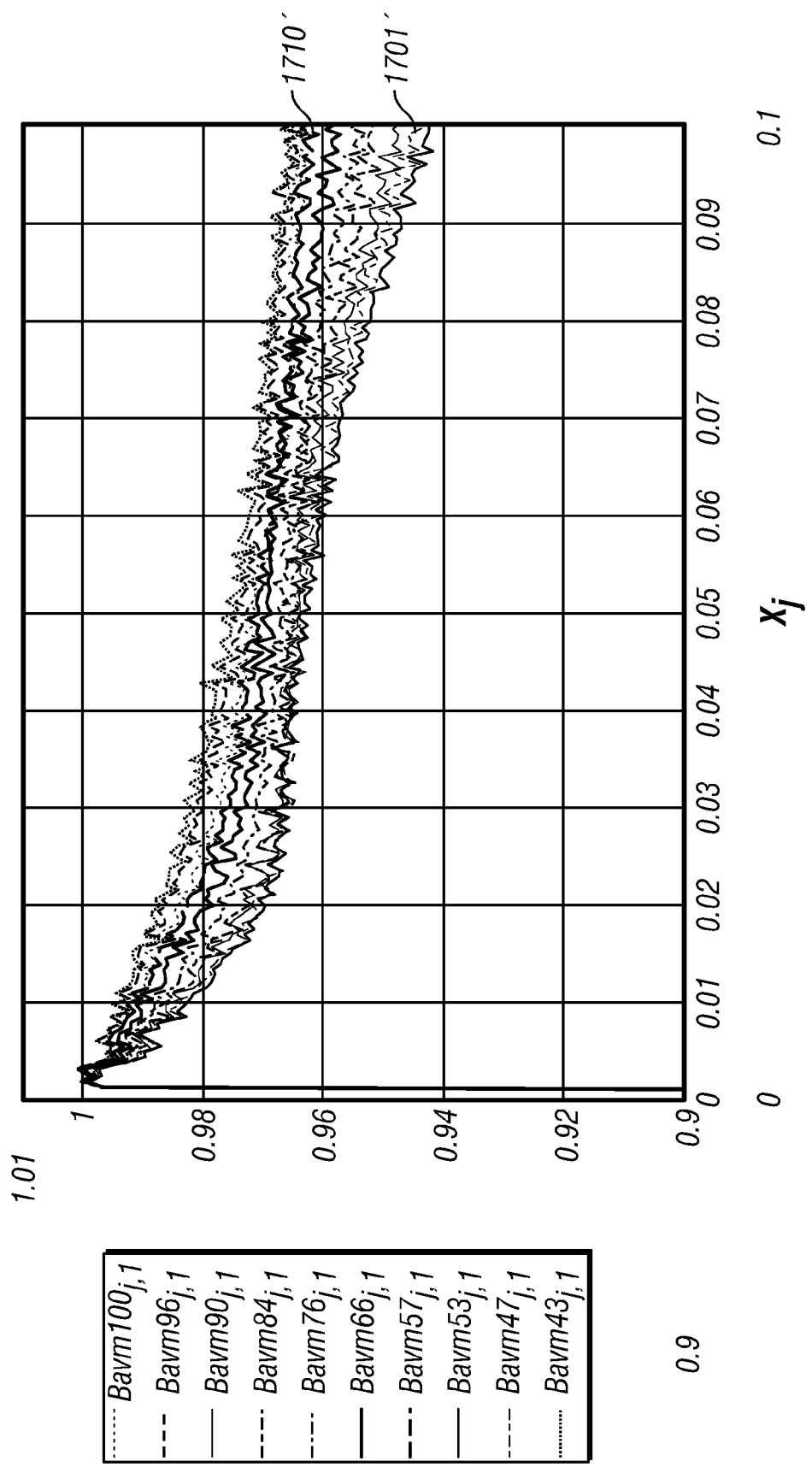
FIG. 17 shows a detail of the simulated echo amplitudes of the averaged echo trains of FIG. 16.

FIG. 16 shows examples of averaged echo trains obtained in this fashion. The curve 1701 corresponds to the fastest average motion of the averaged echo trains with an average velocity of 100 m/h, while 1702, 1703, 1704, 1705, 1706, 1707, 1708, 1709 and 1710 correspond to averaged echo trains with average velocities of 96 m/h, 90 m/h, 84 m/h, 76 m/h, 66 m/h, 57 m/h, 53 m/h, 47 m/h and 43 m/h respectively. FIG. 17 shows a detail of the plots of FIG. 16. To simplify the illustration, only the echo trains corresponding to the fastest 1701' (100 m/h) and the slowest 1710' (43 m/h) average velocity are labeled.

Figure 18:
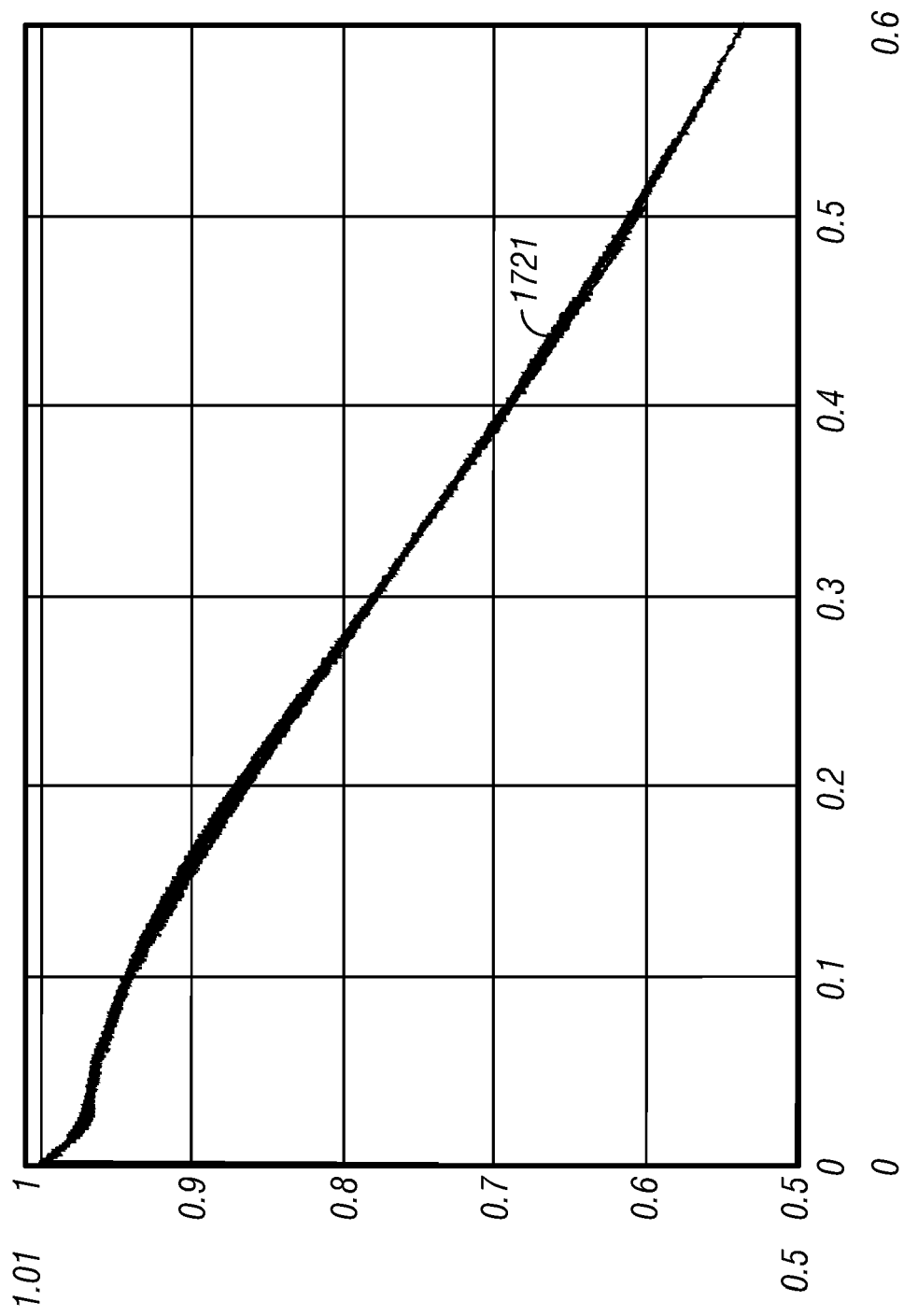
FIG. 18 shows the data of FIG. 16 with the horizontal axis for each trace scaled according to its averaged velocity.
Figure 19:
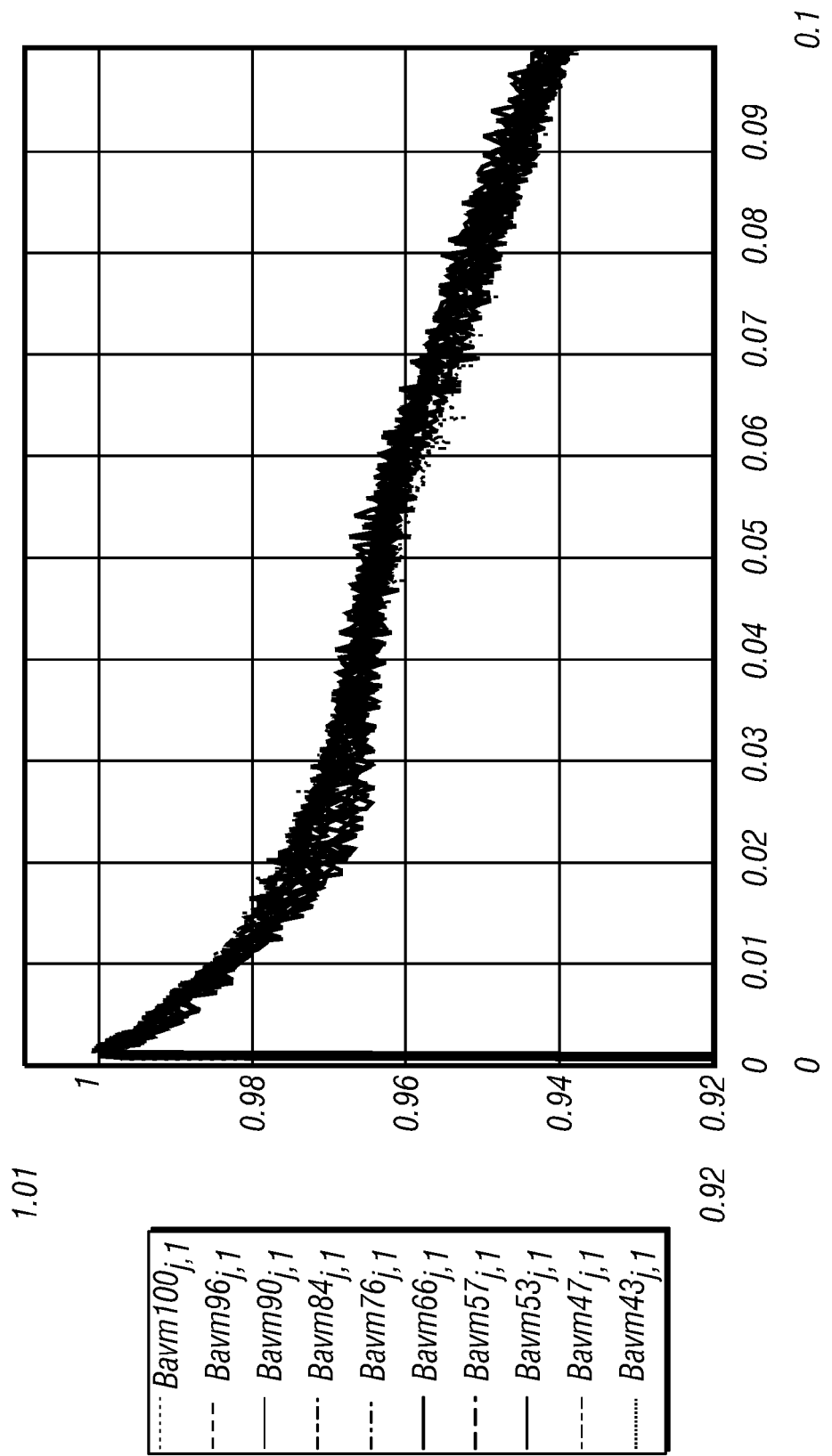
FIG. 19 shows a detail of the echo amplitudes of the averaged echo trains with time scaling of FIG. 18.

Turning now to FIG. 18, the echo trains of FIG. 16 are replotted with the abscissa rescaled by the average horizontal velocity corresponding to the individual echo trains. On this display, the different curves are virtually indistinguishable as denoted by 1721. FIG. 19 some separation between the curves is noticeable.

Figure 20:
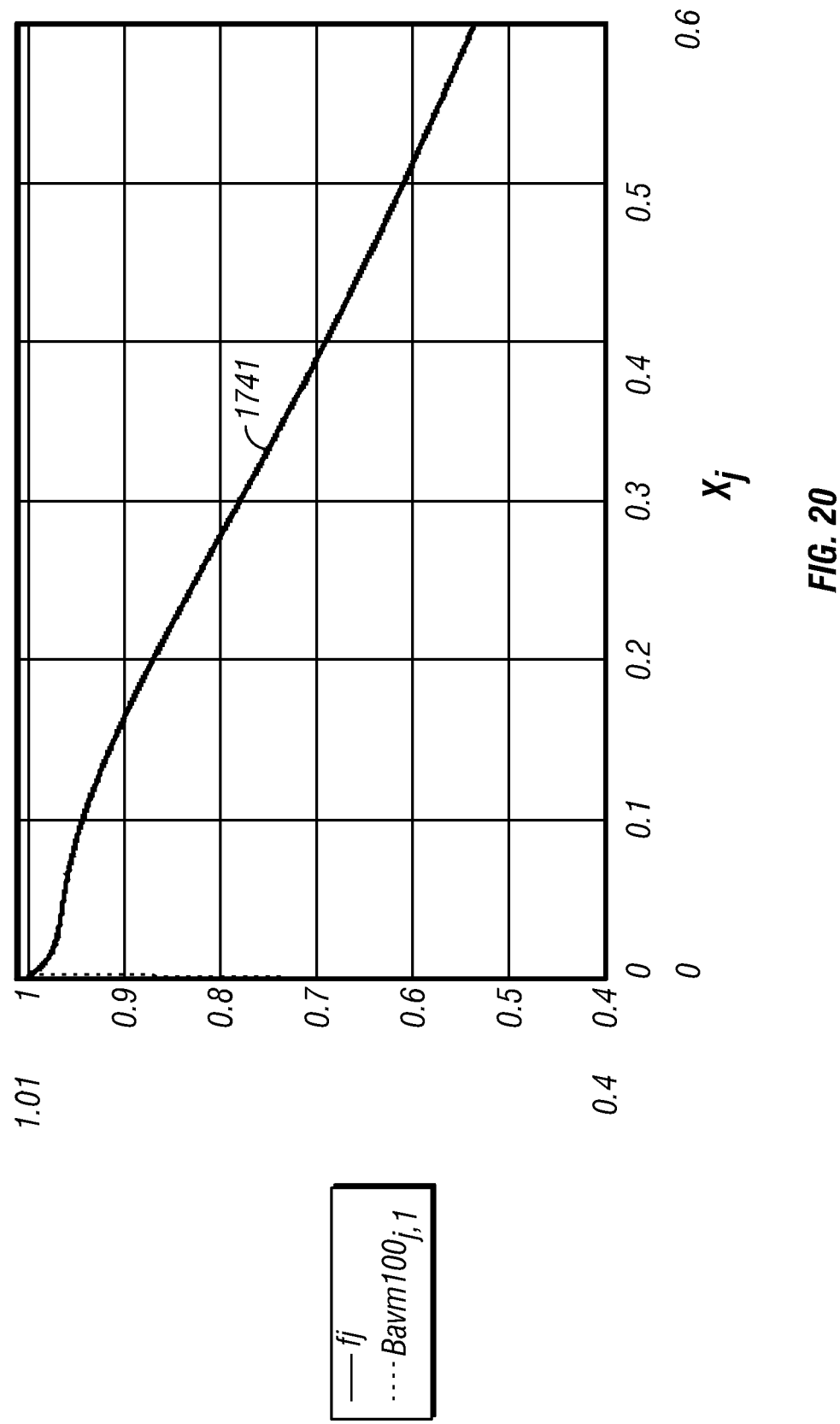
FIG. 20 shows simulated NMR data with an axial velocity of 100 m/h and a fit to the data using a method of the present invention.
Figure 21:
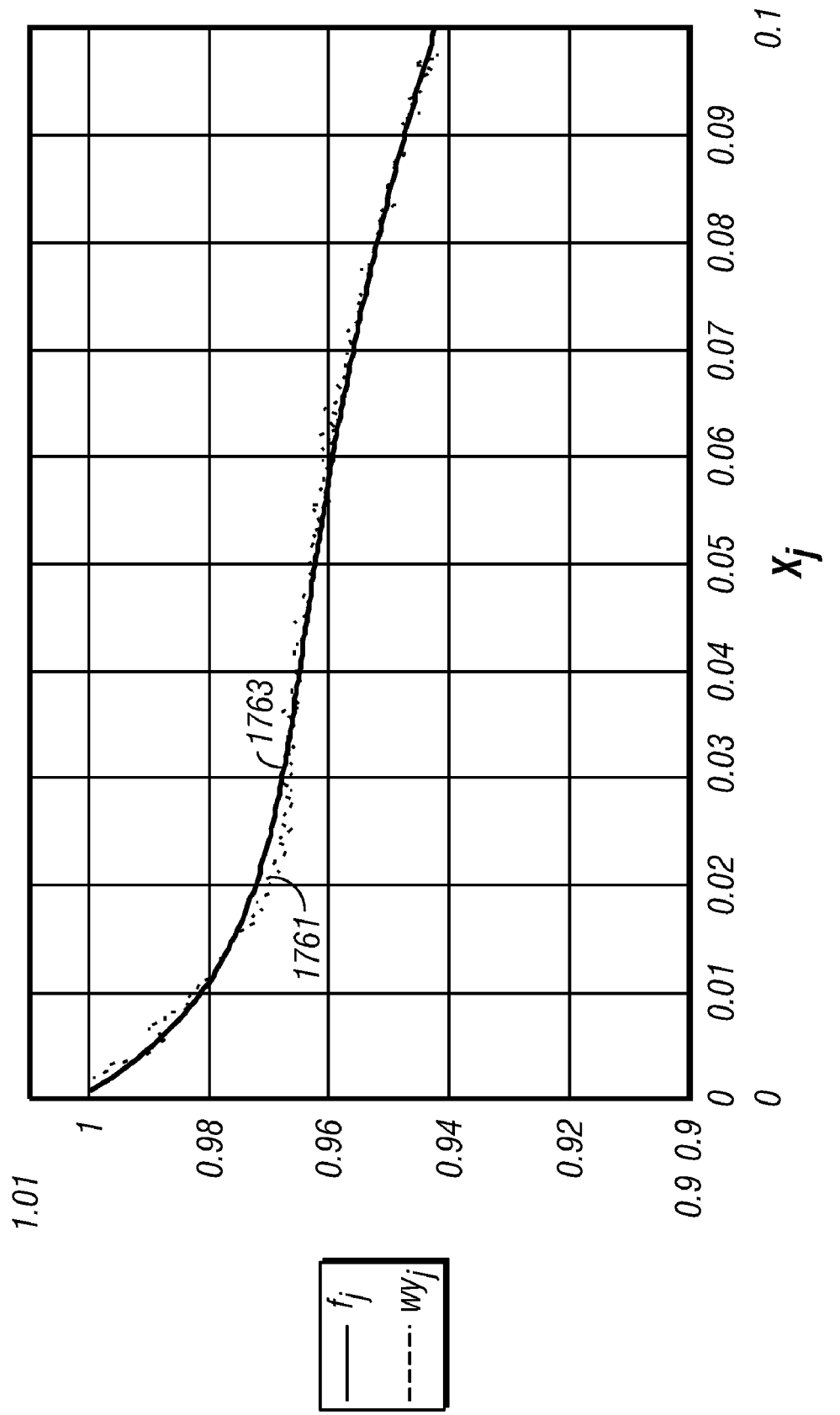
FIG. 21 shows a detail of the plot in FIG. 20.

FIG. 20 shows the result of fitting the average NMR echo train corresponding to an average velocity of 100 m/h with a fifth order polynomial plus an exponential term. The coefficients of the fitting for the exampler are $p_0=0.961$, $p_1=-0.254$, $p_2=-5.551$, $p_3=12.11$, $p_4=-11.99$, $P_5=4.617$, $P_6=0.04$, $P_7=81$;

and the fitted curve is denoted by 1741 in FIG. 20. A detail of FIG. 20 is shown in FIG. 21 where the fit curve is denoted by 1763 and the individual data points by 1761.

Figure 22:
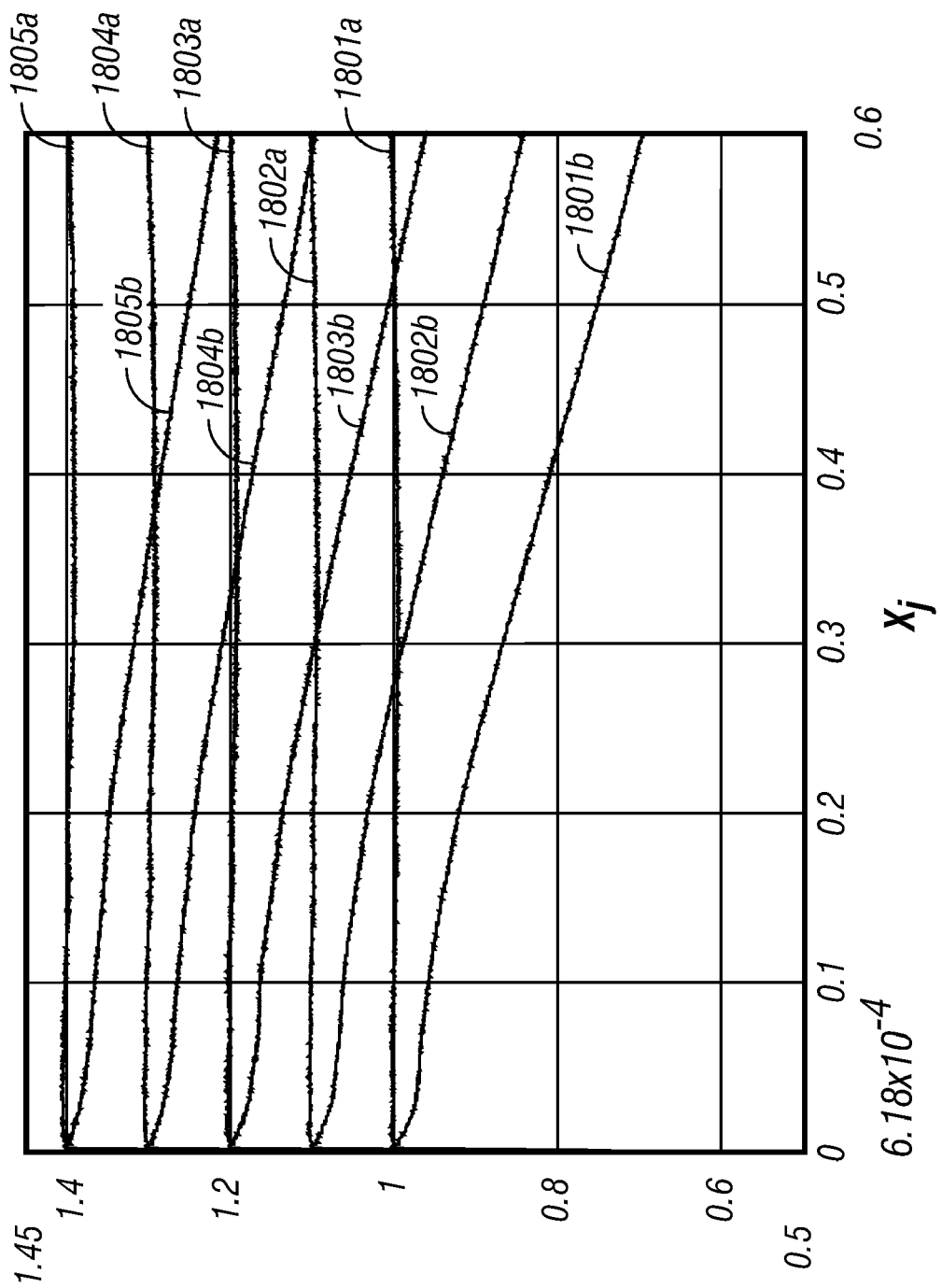
FIG. 22 shows the results of correction using averaged velocities of 43 m/h to 66 m/h.
Figure 23:
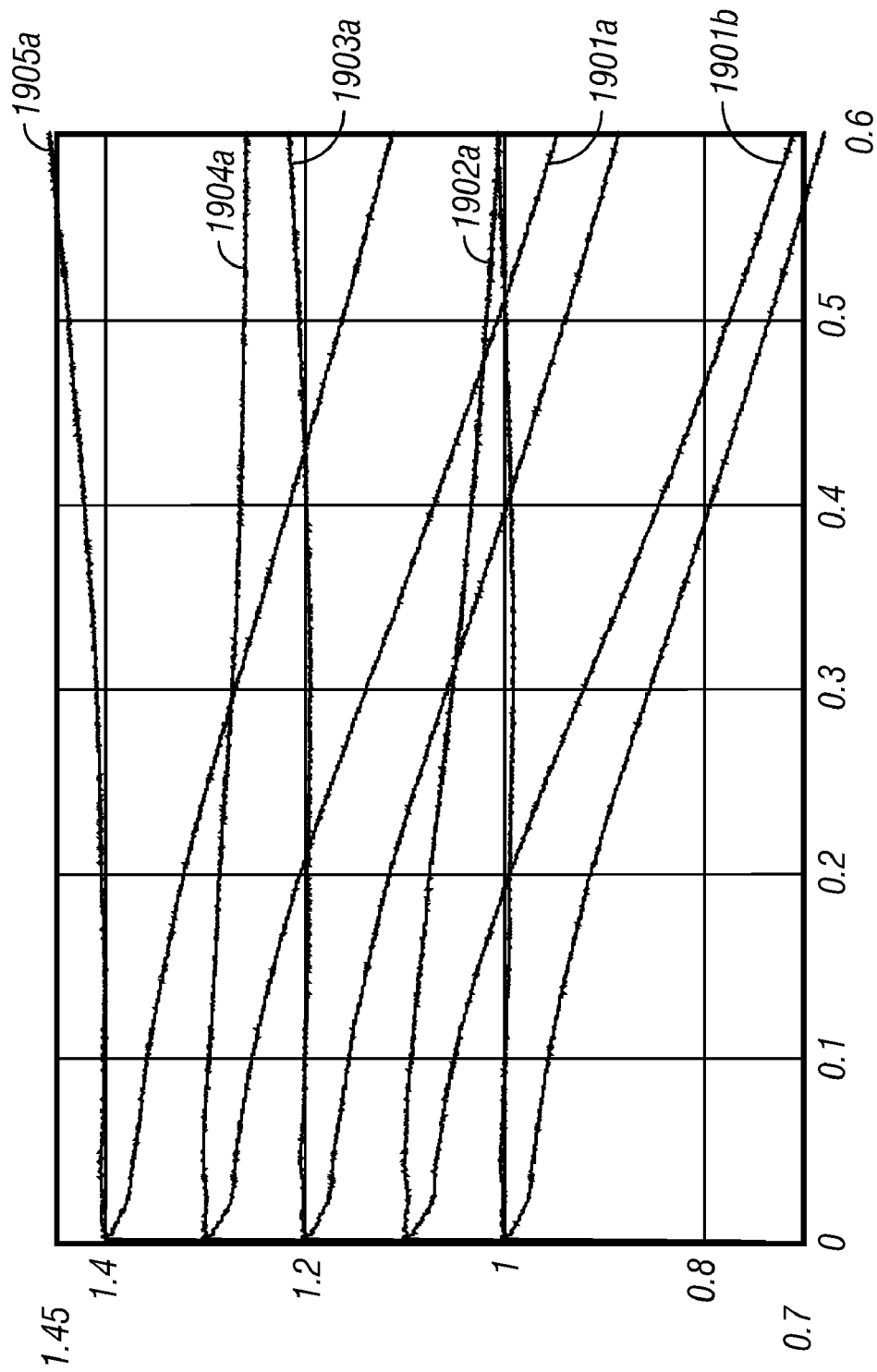
FIG. 23 shows the robustness of the present invention in the presence of porosity variations sampled by different echo trains.

A correction using the average velocity may then be applied to the averaged NMR echo trains in a manner similar to that described above with respect to the individual echo trains. FIG. 22 shows simulations obtained assuming an infinite $T_2$ decay. The uncorrected average echo trains are denoted by 1801b, 1802b, 1803b, 1804b and 1805b for averaged echo trains having an average velocity of 66, 57, 53, 47 and 43 m/h respectively. The corresponding corrected average echo trains are denoted by 1801a, 1802a, 1803a, 1804a and 1805a respectively. As in FIG. 6, vertical offsets are applied to the curves to make the illustration easier to comprehend. As FIG. 22 shows, the corrected traces using the averaged echo trains and the averaged velocity substantially approach the ideal.

A problem may arise with averaging echo trains over an interval (that may be up to 4 minutes in length) if the porosity of the formation is changing during the course of the measurements. To evaluate the effect of this, a simulations were run for the velocities of 20, 40, 60, 90, 100 and 120 m/h resulting in an average velocity of 70 m/h. The NMR echo signals were weighted differently for each velocity, simulating the effect of different porosities in the earth formation. The curves 1901b and 1901a are the uncorrected and corrected average echo trains where the weights are the same, i.e., each echo train yields at its start the same NMR signal amplitude (same porosity). The other curves 1902a, 1903a, 1904a, 1905a shows the results of different weightings of the echo sequences. As might be expected, with the non-uniform weighting, the performance deteriorates somewhat, but the results are significantly better than without the correction. As before, there is an offset between the individual curves to ease the comprehension of the figure.

The Correction B described above may be applied using the averaged velocity (instead of the unaveraged velocity described above). This may be done in addition to or independently of the first correction using the averaged velocity described above.

The processing of the data may be accomplished uphole after the data have been retrieved from the NMR tool's memory, or may be accomplished by a downhole processor. In the latter case the averaged velocity must be available downhole. E.g. the averaged velocity may be obtained uphole and transmitted downhole by a suitable method of telemetry. Implicit in the control and processing of the data is the use of a computer program implemented on a suitable machine readable medium that enables the processor to perform the control and processing. The machine readable medium may include ROMs, EPROMs, EAROMs, Flash Memories and Optical disks.

The invention has been described with reference to a NMR device that is part of a BHA conveyed on a drillstring. The invention is equally applicable for NMR devices conveyed on coiled tubing, wireline, and slickline. The processing described herein may be done using a downhole processor and the results stored on a suitable memory downhole or telemetered to the surface. Alternatively, the data may be stored on a downhole memory and processed when the BHA is tripped out of the borehole. With improved telemetry capability, it should be possible to telemeter the NMR measurements to a surface location and do the processing there.

While the foregoing disclosure is directed to the specific embodiments of the invention, various modifications will be apparent to those skilled in the art. It is intended that all such variations within the scope and spirit of the appended claims be embraced by the foregoing disclosure.

What is claimed is:

1. A method of processing Nuclear Magnetic Resonance (NMR) signals from an earth formation, the method comprising:
    (a) conveying a NMR logging tool into a borehole in said earth formation and moving it axially therein with a velocity;
    (b) polarizing nuclear spins in said earth formation;
    (c) pulsing an antenna on said NMR logging tool with a plurality of pulse sequences, each of the plurality of pulse sequences producing an associated echo train;
    (d) averaging the plurality of echo trains to give an averaged echo train;
    (e) correcting the averaged echo train using a function of an average of the velocity and producing a corrected echo train; and
    (f) recording the corrected echo train on a suitable medium.

2. The method of claim 1 further comprising conveying the logging tool into said borehole on one of (i) a wireline, and, (ii) a slickline, (iii) a drillstring, and, (iv) coiled tubing.

3. The method of claim 1 wherein said correcting further comprises scaling the averaged echo train by a normalizing function related the average velocity and a reference velocity.

4. The method of claim 2 wherein said correcting further comprises using an equation of the form $$A_{cor}(t) = \frac{A(t)}{f_c\left(t \cdot \frac{V_{axial}}{V_{ref}}\right)}$$

wherein A(t) is one of (i) an in-phase component of the averaged echo train, (ii) a quadrature component of the averaged echo train, and, (iii) an amplitude of the averaged echo train, t is a time, $A_{cor}(t)$ is a corrected signal, $V_{axial}$ is the average velocity, and $V_{ref}$ is the reference velocity, and $f_c$ is said normalizing function.

5. The method of claim 4 wherein said function $f_c$ comprises a polynomial function and a perturbing term.

6. The method of claim 5 wherein said perturbing term comprises an exponential term.

7. The method of claim 1 wherein an excitation pulse of the plurality of pulse sequences has a tip angle that is substantially equal to 90°.

8. The method of claim 1 wherein said at least one pulse sequence comprises a plurality of pulse sequences with a wait time TW between an ending time of a pulse sequence and a starting time of a subsequent pulse sequence.

9. The method of claim 1 further comprising using a saturation sequence before a pulse sequence of said plurality of pulse sequences.

10. The method of claim 1 wherein said correcting further comprises scaling the averaged echo train by a normalizing function related to the average velocity, a longitudinal relaxation time of the earth formation, a reference velocity and a wait time.

11. The method of claim 9 wherein said correcting further comprises scaling the averaged echo train by a normalizing function related to the average velocity, a longitudinal relaxation time of the earth formation, a reference velocity and a wait time.

12. The method of claim 1 wherein said logging tool is conveyed in said borehole on a bottom hole assembly (BHA), the method further comprising measuring the velocity at a surface location.

13. The method of claim 1 wherein said nuclear spins are characterized by a transverse relaxation time ($T_2$) distribution and a longitudinal relaxation time ($T_1$) distribution, the method further comprising estimating a porosity of the earth formation using the average velocity, an estimate of the $T_2$ distribution and an estimate of the $T_1$ distribution.

14. An apparatus for Nuclear Magnetic Resonance (NMR) logging of an earth formation, the apparatus comprising:

(a) a NMR logging tool configured to be conveyed into a borehole in said earth formation by a conveyance device and moved axially therein with a velocity of motion;

(b) a magnet on said NMR logging tool configured to polarize nuclear spins in the earth formation;

(c) an antenna on said logging tool configured to be pulsed with a plurality of pulse sequences, each of the plurality of pulse sequences producing an associated echo train;

(d) a receiver configured to receive said spin echo signals; and (e) a processor configured to:

(A) average the plurality of echo trains to produce an averaged echo train;

(B) correct the averaged echo train using a function of an average of the velocity, and produces a corrected echo train; and (C) record the corrected echo train on a suitable medium.

15. The apparatus of claim 14 wherein said conveyance device is selected from the group consisting of (i) a wireline, and, (ii) a slickline, (iii) a drillstring, and, (iv) coiled tubing.

16. The apparatus of claim 14 wherein said processor is configured to correct said spin echo signals using a normalizing function related to the average of the velocity and a reference velocity.

17. The apparatus of claim 15 wherein said processor is configured to correct said spin echo signals using an equation of the form $$A_{cor}(t) = \frac{A(t)}{f_c\left(t \cdot \frac{V_{axial}}{V_{ref}}\right)}$$

wherein $A(t)$ is one of (i) an in-phase component of the averaged echo train, (ii) a quadrature component of the averaged echo train, and, (iii) an amplitude of the averaged echo train, t is a time, $A_{cor}(t)$ is a corrected signal, $V_{axial}$ is the average of the velocity, and $V_{ref}$ is the reference velocity, and $f_c$ is the normalizing function.

18. The apparatus of claim 14 wherein said nuclear spins are characterized by a transverse relaxation time ($T_2$) distribution and a longitudinal relaxation time ($T_1$) distribution, and wherein said processor is further configured to estimate a porosity of said earth formation, based in part on the average of the velocity, an estimate of the $T_2$ distribution and an estimate of the $T_1$ distribution.

19. A computer readable medium for use with an apparatus for Nuclear Magnetic Resonance (NMR) logging of an earth formation, the apparatus comprising:

(a) a NMR logging tool configured to be conveyed into a borehole in said earth formation by a conveyance device and moved axially therein with a velocity of motion;

(b) a magnet on said NMR logging tool configured to polarize nuclear spins in the earth formation;

(c) an antenna on said logging tool configured to be pulsed with a plurality of pulse sequences, each of the plurality of pulse sequences producing an associated echo train; and (d) a receiver configured to receive said spin echo signals; the medium including instructions that enable a processor to (e) average the plurality of echo trains to produce an averaged echo train;

(f) correct the averaged echo train using a function of an average of the velocity, and produces a corrected echo train; and (g) record the corrected echo train on a suitable medium.

20. The medium of claim 19 further comprising at least one of (i) a ROM, (ii) an EPROM, (iii) an EAROM, (iv) a flash memory, and (v) an optical disks.

* * * * *